US010837898B2

(12) United States Patent
Joch et al.

(10) Patent No.: US 10,837,898 B2
(45) Date of Patent: Nov. 17, 2020

(54) SENSOR FOR A VIRTUALLY SIMULTANEOUS MEASUREMENT OF A TRANSMISSION AND/OR FORWARD SCATTERING AND/OR REMISSION AND FOR A SIMULTANEOUS MEASUREMENT OF THE TRANSMISSION AND FORWARD SCATTERING OR TRANSMISSION AND REMISSION OF A LIQUID SAMPLE

(71) Applicant: BASF COATINGS GMBH, Muenster (DE)

(72) Inventors: Andreas Joch, Muenster (DE); Michael Schaefer, Altrip (DE); Carlos Arthur Leaes Peixoto, Sao Bernardo do Campo (BR); Juergen Ettmueller, Ludwigshafen (DE); Stefan Ziegler, Ludwigshafen (DE); Pieter Moonen, Muenster (DE)

(73) Assignee: BASF COATINGS GMBH, Münster (DE)

( * ) Notice: Subject to any disclaimer, the term of this patent is extended or adjusted under 35 U.S.C. 154(b) by 0 days.

(21) Appl. No.: 16/333,146

(22) PCT Filed: Sep. 7, 2017

(86) PCT No.: PCT/EP2017/072427
§ 371 (c)(1),
(2) Date: Mar. 13, 2019

(87) PCT Pub. No.: WO2018/050527
PCT Pub. Date: Mar. 22, 2018

(65) Prior Publication Data
US 2019/0212256 A1 Jul. 11, 2019

(30) Foreign Application Priority Data
Sep. 13, 2016 (EP) .................................. 16188515

(51) Int. Cl.
*G01J 3/28* (2006.01)
*G01N 21/25* (2006.01)
(Continued)

(52) U.S. Cl.
CPC ............ *G01N 21/251* (2013.01); *G01J 3/501* (2013.01); *G01J 3/524* (2013.01); *G01N 1/2035* (2013.01);
(Continued)

(58) Field of Classification Search
CPC .. G01N 21/251; G01N 21/255; G01N 21/534; G01N 33/32; G01N 21/0303; G01N 15/02; G01J 3/524; G01J 3/501
See application file for complete search history.

(56) References Cited

U.S. PATENT DOCUMENTS 3,826,364 A * 7/1974 Bonner ................. B07C 5/3425
209/3.1
6,040,913 A 3/2000 Johnson
(Continued)

FOREIGN PATENT DOCUMENTS

DE 2361752 A1 6/1974
EP 472899 A1 3/1992
(Continued)

OTHER PUBLICATIONS

European Search Report for EP Patent Application No. 16188515.7, dated Mar. 15, 2017, 3 pages.
(Continued)

*Primary Examiner* — Abdullahi Nur
(74) *Attorney, Agent, or Firm* — Armstrong Teasdale LLP

(57) ABSTRACT

Described herein is a sensor for a virtually simultaneous measurement of transmission and/or forward scattering and/ or remission and for a simultaneous measurement of the transmission and forward scattering or the transmission and
(Continued)

remission of a liquid sample. Further described herein is a method for a virtually simultaneous measurement of transmission and/or forward scattering and/or remission and for a simultaneous measurement of the transmission and forward scattering or the transmission and remission of a liquid sample using a sensor according to the invention. Further described herein is a method for using the sensor according to the invention in order to determine the color properties of painting agents such as lacquers, dyes, pastes, and pigments or dilutions thereof.

19 Claims, 13 Drawing Sheets

(51) Int. Cl.

| | | |
|---|---|---|
| | *G01N 21/53* | (2006.01) |
| | *G01N 1/20* | (2006.01) |
| | *G01N 21/05* | (2006.01) |
| | *G01N 21/03* | (2006.01) |
| | *G01N 21/47* | (2006.01) |
| | *G01J 3/50* | (2006.01) |
| | *G01J 3/52* | (2006.01) |
| | *G01N 33/32* | (2006.01) |
| | *G01N 21/17* | (2006.01) |

(52) U.S. Cl.
CPC ......... *G01N 21/0303* (2013.01); *G01N 21/05* (2013.01); *G01N 21/255* (2013.01); *G01N 21/4785* (2013.01); *G01N 21/53* (2013.01); *G01N 21/532* (2013.01); *G01N 21/534* (2013.01); *G01N 33/32* (2013.01); *G01N 2021/036* (2013.01); *G01N 2021/1738* (2013.01); *G01N 2021/4707* (2013.01); *G01N 2021/4709* (2013.01); *G01N 2021/4711* (2013.01); *G01N 2201/0668* (2013.01); *G01N 2201/06146* (2013.01); *G01N 2201/08* (2013.01)

(56) References Cited

U.S. PATENT DOCUMENTS

| | | | |
|---|---|---|---|
| 6,288,783 B1 | 9/2001 | Auad | |
| 2008/0273204 A1 | 11/2008 | Peixoto et al. | |
| 2016/0202164 A1* | 7/2016 | Trainer | G01N 15/0211 356/336 |

FOREIGN PATENT DOCUMENTS

| | | |
|---|---|---|
| EP | 932829 A1 | 8/1999 |
| EP | 932829 B1 | 9/2008 |
| GB | 796745 A | 6/1958 |
| WO | 2000045152 A1 | 8/2000 |
| WO | 2005003740 A1 | 1/2005 |
| WO | 2005062022 A1 | 7/2005 |
| WO | 2009065613 A1 | 5/2009 |
| WO | 2013173401 A1 | 11/2013 |

OTHER PUBLICATIONS

English Translation of International Search Report for International Patent Application No. PCT/EP2017/072427, dated Nov. 21, 2017, 3 pages.

* cited by examiner

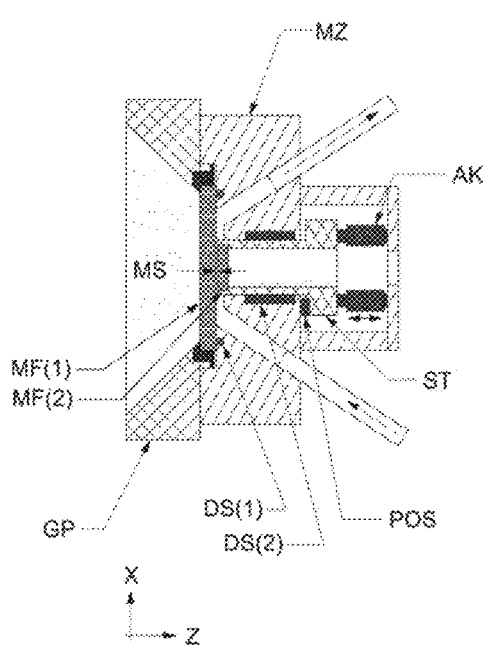
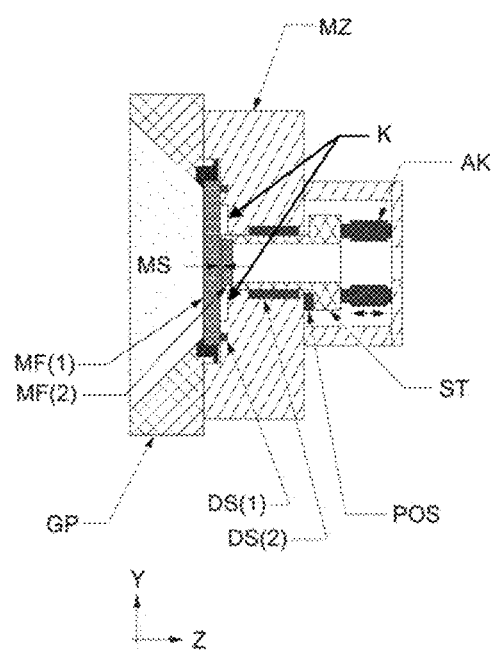
FIG. 2c
FIG. 2d

SENSOR FOR A VIRTUALLY SIMULTANEOUS MEASUREMENT OF A TRANSMISSION AND/OR FORWARD SCATTERING AND/OR REMISSION AND FOR A SIMULTANEOUS MEASUREMENT OF THE TRANSMISSION AND FORWARD SCATTERING OR TRANSMISSION AND REMISSION OF A LIQUID SAMPLE

CROSS-REFERENCE TO RELATED APPLICATIONS

This application is the national stage entry of PCT/EP2017/072427, filed on Sep. 7, 2017, which claims the benefit of priority to European Patent Application No. 16188515.7, filed Sep. 13, 2016, each of which is incorporated by reference in its entirety herein.

The present invention relates to a sensor for quasi-simultaneous measurement of the transmission and/or forward scattering and/or re-emission of a liquid sample and for simultaneous measurement of the transmission and forward scattering or transmission and re-emission of a liquid sample, a process for quasi-simultaneous measurement of the transmission and/or forward scattering and/or re-emission of a liquid sample, and for simultaneous measurement of the transmission and forward scattering or transmission and re-emission of a liquid sample using a sensor according to the invention, and the use of the sensor according to the invention for quasi-simultaneous measurement of the transmission and/or forward scattering and/or re-emission of a liquid sample, and for simultaneous measurement of the transmission and forward scattering or transmission and re-emission of a liquid sample for determining the color properties of painting means such as coatings and colors, pastes and pigments or the dilutions thereof.

Background

Since the creation of a color impression is physically a complex process, the terms used will be explained first.

Fundamental distinction is to be made between self-illuminating objects (for example lamps, display screens, illuminated areas) and objects which need to be illuminated for observation. In this case, either the object is shone through and the light passing through is observed (technical term: transmission), or it is irradiated with incident light and the reflected light is observed (technical term: re-emission). "Colored" refers to preparations which partially absorb visible light.

Forward scattering relates in general to scattering processes in which deviation of light in the forward direction takes place. Forward scattering thus differs from, inter alia, transmission by deviation through a scattering angle θ, the scattering angle generally being defined as the angle by which the scattered light is deviated after interaction with a particle. In the context of the invention, forward scattering (VS) thus refers to scattering processes in which deviation of the light in the forward direction takes place in the scattering angle range between >0° and 90°, and which are not regarded as transmission. In general, forward scattering permits determination of the size and isotropy of particles.

Quasi-back scattering, in which as a consequence of diffuse light propagation in the dispersive medium light is scattered back again in the incoming radiation direction, i.e. at a scattering angle of 180°, should be distinguished from forward scattering; it is merely listed here for the sake of completeness. This single-angle back scattering measurement/quasi-back scattering measurement contains virtually no information relating to the size and isotropy of particles.

The terms "transparent" and "diffusely scattering" are clear. Known objects which may be cited here are on the one hand colorless or colored clear films or disks as examples for "transparent", and on the other hand opaque films (for example paper) or frosted glass as examples for "diffusely scattering".

Coloring preparations likewise differ according to this aspect, and reference is made for example to covering or transparent colors. The latter require a scattering, most preferably white, background in order to make the color visible, for example paper, plastic film or textile material. Covering preparations produce a colored surface without the background shining through (for example oil paints, automobile paints, wall paints) and are composed either of mixtures of scattering pigments (white pigments, for example $TiO_2$) and absorbing constituents (non-scattering or weakly scattering color pigments and/or soluble absorbing components), or of pigments which both scatter and absorb.

In the industrial production of colored preparations, the customer expects the product delivered according to a specification always to produce the same color after use.

The color in the sense of re-emission and the hiding power are thus part of the product specification. Expressed simply, when applied with the film thickness a person skilled in the art would deem normal, the coating should achieve the same color on a black background and on a white background.

For the observation of colors, it is necessary to explain the term colorimetry. There are a plurality of technical possibilities for carrying this out. The results thereby obtained are in principle transferable and comparable, even if they are not always of the same detail resolution. Colorimetry may be defined by using DIN standard 5033. Measurement in the wavelength range of visible light, from 380 nm to 780 nm, is conventional, although a smaller wavelength range is sometimes also observed.

Colorimetry is based on the average human capacity of distinguishing between homogeneous color surfaces lying directly next to one another. The human eye can only distinguish between three color stimuli, namely red, green and blue. These sensitivity ranges are technically referred to as X, Y and Z, and do not entirely coincide with the spectra of additive color mixture with R, G and B, for example in televisions and computer screens.

Essentially two solutions are conventional for colorimetry, on the one hand detectors with filters, and on the other hand systems with a wavelength-dispersive element in the beam path, which images the resolved spectrum onto a linear diode array or linear CCD array.

For the variant with filters and detectors, there are the following obvious embodiments:
  3 regions with X, Y, Z or R, G, B filters and 3 detectors
  n ranges with n narrowband filters and n detectors.

For the variant with a wavelength-dispersive element, variants with 128, 256, 512, 1024 or more detection ranges are typically used. A smaller required wavelength resolution is achieved by combining adjacent channels. These data reduction methods are known to the person skilled in the art.

In principle, the reverse approach is also possible, namely that the reception is carried out with a broadband detector which is sensitive in the entire wavelength range examined, and the wavelength selection is carried out on the illumination side by 3 or more different light sources being switched on successively in a similar way to the wavelength ranges described above or a white light source being coupled to a wavelength-dispersive element.

Colorimetry which addresses only 3 wavelength ranges is often sufficient. The most accurate measurements are offered by measuring devices which subdivide the entire visible spectrum into very narrow ranges, for example wavelengths of 2-20 nm.

For the scientific description of colored preparations, the terms scattering (S) and absorption (K or A) have become established for characterization of coloring substances as a reference for all theories and formulae which describe the color of colored layers, the Kubelka-Munk theory known to the person skilled in the art may be mentioned here, which calculates the intensity at the observation wavelength A reflected (re-emission $R(\lambda)$) or transmitted (transmission $T(\lambda)$) by a layer of given thickness (d) irradiated with white light.

It has previously been prior art that these calculations can only be carried out for isotropically acting pigments and colorants. Scientific approaches by which this can also be calculated for arbitrary colorants with for example special-effect pigments are not yet publicly available.

Calculations for determining the properties of the resulting mixed product from known conventional pigment properties have been published, and are also used in practice.

Likewise, prior art are methods for determining the scattering and absorption properties of the product from measurements of mixtures of the product with known reference materials (white and black pastes).

As an alternative, it is also possible, starting with standard samples of the product, to dose known amounts of the product components therewith and to register the effects in the form of concentration series. On the basis of such data, it is then possible to interpret a deviation of the color of a product batch as a deviation of the formulation and correct it accordingly.

With various mathematical inversion methods, it is also possible to develop calculation methods for determining the properties and/or concentrations of the individual components of the preparation from the measured properties of the pigment preparation.

Although the properties of infinitesimally thin layers of pigments can be described for all colorants (for example Mie theory, or discrete dipole approximation), it is not prior art to calculate the multiple scattering of layers with a thickness close to that used in practice (i.e. not infinitesimally thin layers).

During the production of all types of coatings, it is at any time possible to take a sample, prepare a sample plate therefrom, dry it and optionally also heat-treat (bake) it, and measure the resulting color. From the deviations from the agreed "standard" reference color, it is then possible to determine correction steps. In this case, the hue achieved and the hiding power achieved are two independent specifications respectively to be adjusted. In order to explain the problem a color which consists of a mixture of white pigment and a colored pigment may be considered. If the mixing ratio of white and color is incorrect, the color becomes too pale or too intense, or dark. It is known to the person skilled in the art that, pursuant to Kubelka-Munk, the color depends only on the ratio K/S of the absorbing component to the scattering component, but when the preparation contains too little of both the required hiding power is not achieved (the background then shows through for the user).

For safety, therefore, more pigment than necessary is often added to the formulations or dosed in order to err on the side of caution even in the event of unavoidable variations in the quality of the starting products, the production process and the application process and therefore fully meet the customer specifications.

Particularly for coatings in the low price range (for example coatings for buildings), however, this is disadvantageous because expensive pigments are therefore dosed more highly than is necessary for the desired color effect, and, additionally, the other properties of the product may sometimes be detrimentally affected.

The determination and the quality monitoring of effect pigments or liquid effect pigment preparations, for example of Al and mica pigments as are used in the field of coatings and paints, are likewise generally difficult and costly and inconvenient. For complete characterization, the particle size, the angle-dependent color of the particles and the general colour impression must be registered.

Hence, there is a need for a measurement instrument which renders it possible to determine the color properties such as color locus, hiding power and color strength (see, for example, Römpp Lexikon, Georg Thieme Verlag) of liquid samples, that is to say of individual components or of a ready product mixture, i.e. of painting means such as coatings and colors, pastes and pigments, as easily and quickly as possible with a high measurement accuracy.

US2008/0273204 A1 relates to an apparatus and a process for measuring the transmission and re-emission of a liquid sample, in particular of a paint or another opaque liquid, comprising a referenced light source 1, a beam splitter 18 ("switch"), a passable measurement cell 11 comprising an adjustable measurement gap ([0110]), at least one reception optical unit and at least one detector, and also a lock-in amplifier 5 which should significantly improve the signal-to-noise ratio. Here the light flux originating from the light source 1 by way of an optical fiber 10 may be split by a beam splitter 18, as a result of which a simultaneous or separate measurement of re-emission and transmission is possible. By shifting the position of the beam splitter 18, illumination angle and hence also re-emission angle are adjustable ([0126]). It is likewise possible to register the forward scattering ("second transmitted electromagnetic radiation") at an angle of 45° ([0127]).

EP 0 472 899 A1 relates to a photometric apparatus for measuring the degree of damping in the case of light propagation in dispersive systems, comprising a passable cuvette (1), a light source (4), at least one illumination optical unit in the form of optical waveguides (LWL), and at least one reception optical unit in the form of optical waveguides (LWL), wherein transmission and re-emission or transmission and quasi-back scattering may be registered simultaneously by selecting the number of fibers and the arrangement in the optical waveguides and the type of coupling into the cuvette, for example at an angle of 45° or through a put-on glass plate (Gp) with a thickness of 400 to 700 µm for the re-emission measurement.

WO2005/003740 has disclosed a re-emission sensor for measuring a liquid sample, formed from a) an optics unit (A), which comprises a light source (Aa) in the form of a lamp and a fiber optic comprising light waveguides (Ab), at least one light waveguide being a reference guide, and b) a sample analysis unit (B), which comprises a measurement window (Ba) and a sample analysis cell (Bb), wherein the optics unit is arranged on one side of the one measurement window and the sample analysis cell is arranged on the other side of the same measurement window, by pressing the latter onto the measurement window in such a way that a gap, through which a sample to be measured in the form of a liquid pigment preparation must pass, is formed between the measurement window and the sample analysis cell, the passage through the gap leading to significant shearing of the sample, and c) a system control unit (C) comprising detectors (Ca) for recording measurement data and an evaluation device (Cb) connected thereto, wherein at least one light waveguide connection is fed from the light source (Aa) to the measurement window (Ba) and from the measurement window (Ba) further to the detector (Ca) in order to generate a measurement signal (re-emission of the product), and at least one reference guide connection is fed directly from the light source (Aa) to the detector (Ca) or from the measurement window (Ba) to the detector (Ca) in order to generate a reference signal (internal reflection).

In addition to the above-described re-emission sensor (WO2005/003740), WO2005/062022 discloses a three-dimensional flow cell for aligning non-isometric particles in a liquid sample along two axes and the use thereof with a re-emission sensor. In principle, the option of measuring transmission or quasi-back scattering using the photometric measurement device is also mentioned.

U.S. Pat. No. 6,040,913 and WO 00/45152 relate to a process for determining the scattering efficiency of a white pigment, wherein the light scattering efficiency is correlated with performance in final use, comprising the production of a dilute suspension of a pigment in a liquid medium with a known concentration of the pigment in the suspension, measurement of the total transmission (T) of the suspension at a wavelength of at least 600 nm, conversion of the transmission measurement (T) into the optical density (OD) by the equation: OD=−log (T), and division of the optical density by the concentration of the pigment in the suspension in order to determine the light-scattering intensity of the pigment.

WO 2013/173401 relates to a process for measuring one or more properties of a liquid, comprising:

production of a thin film of a sample of the liquid with a predetermined film thickness in the range of from 0.05 mm to 2 mm by using a thin-film component comprising:

C1:

(a) a circular planar disk (101) containing a first surface (101a) and a second disk surface (101b) on the opposite sides of the circular planar disk, the circular planar disk being connected to a rotating shaft (120) connected to a rotationally symmetrical axis (110) of the circular planar disk perpendicular to the disk surfaces, in order to allow rotation of the circular planar disk;

(b) a component frame (121) which positions the circular planar disk and the rotation shaft;

(c) a thickness control element (125) containing a film setting edge (125a) connected to a liquid return channel (125b) and at least one frame connector (125c), which connects the film setting edge (125a) and the liquid return channel (125b) to the component frame (121), the frame connector being movable in relation to the component frame; and (d) a movement element (130) connected to the rotation shaft in order to allow rotation of the rotation shaft (120) and a movement control element (131) for controlling the rotational speed of the rotation element, rotational direction of the rotation element, or a combination of the two, wherein the thickness control element (125) is positioned on the first surface side (101a) of the circular planar disk (101), the film setting edge (125a) is positioned essentially parallel to the first surface, and the film setting edge (125a) overlaps with the circular planar disk, the latter covering a range of from 50% to 99% of the radius of the circular planar disk (101);

wherein the distance (127) between the film setting edge (125a) and the first surface (101a) lies in the range of from 0.05 to 5 mm and can be adjusted by means of the frame connector; and wherein the predetermined film thickness is controlled by this distance (127) and by the rotational speed and direction;

C2:

measurement of the thin film with one or more measuring devices in order to obtain sample data; and

C3:

Adjusting the one or more properties on the basis of the sample data.

EP 0 932 829 relates to an analysis system for analyzing the physical properties of coatings, pigment pastes or similar systems, which is formed from a device for forming a film of the coatings, pigment pastes and similar systems with a specific thickness, a light source for irradiating the coating to be studied or the pigment paste or similar systems to be studied, wherein an interaction between the light and the coating, the pigment paste or similar systems takes place, wherein a measurement signal is generated; and a device for recording the measurement signal as well as a detector connected to the device for recording the measurement signal.

WO 2009/065613 A1 relates to a device for establishing the particle concentration, the particle size, the mean particle size and the particle size distribution of particles of a dispersive phase, and the turbidity thereof, by measuring the transmission and/or by measuring the scattered light of a measurement beam after passing over a defined measurement path within the dispersive system, wherein depositions at the measurement beam emission surface and measurement beam collector surface are largely avoided.

U.S. Pat. No. 6,288,783 B1 relates to a fluid analysis system for analyzing a specified physical property of a fluid and to a method for same, wherein the system has a film forming means to form a fluid film with a certain thickness, a film irradiation device that is suitable for irradiating the film with electromagnetic radiation to produce interaction radiation, a receptor for receiving the interaction radiation and a detector assigned to the receptor for capturing the interaction radiation. Moreover, at least one of the opposing fluid contact surfaces is transmissive to electromagnetic radiation and the system has a surface cleaning installation.

The measurement arrangements from the prior art have an insufficient measurement accuracy, speed and option for carrying out a plurality of highly accurate spectrometric examinations on a liquid sample.

The available prior art has not solved the problem of reliable registration of spectrometric measurement data for ascertaining the color properties such as color locus, hiding power and color strength, or absorption (K or A) and scattering (S), of liquid samples, i.e. of individual components or a ready product mixture, i.e. of painting means such as coatings and colors, pastes and pigments, with high accuracy and sufficient speed. In particular, a measurement apparatus permitting a complete characterization of angle-dependent particles such as, for example, titanium dioxide or Al- or mica-effect pigments is lacking. Nor has the prior art solved the problem of continuous registration of spectrometric measurement data with high accuracy and sufficient speed for a liquid sample, in particular a flowing liquid sample.

Detailed Description

In order to solve the aforementioned problem, a sensor for quasi-simultaneous measurement of the transmission and/or forward scattering and/or re-emission of a liquid sample, and for simultaneous measurement of the transmission and forward scattering or transmission and re-emission of a liquid sample was found, wherein the sensor is formed from a) one or more light sources (LQ), preferably two light sources (LQ) (TM/VS) and (LQ) (REM), b) one or more illumination optical units (BO), preferably two illumination optical units (BO) (TM/VS) and (BO) (REM), c) at least one measurement cell (MZ), d) at least one reception optical unit (EO) (TM/VS/REM), e) at least one detector (DET) (TM/VS/REM) for measuring transmission signals generated by transmission, for measuring forward scattering signals generated by forward scattering and for measuring re-emission signals generated by re-emission, wherein the measurement cell (MZ) is a cell which can be flowed through and which comprises two opposing measurement windows (MF1) and (MF2) arranged parallel, which are arranged with respect to one another in such a way that a measurement gap (MS), which is filled with the sample to be measured, is formed between the measurement windows, the measurement windows having a defined separation from one another which is variably adjustable during the through-flow operation.

The novel sensor for quasi-simultaneous measurement of the transmission and/or forward scattering and/or re-emission of a liquid sample, and for simultaneous measurement of the transmission and forward scattering or transmission and re-emission of a liquid sample is also referred to as sensor according to the invention below. Preferred embodiments of the sensor according to the invention emerge from the following description and the dependent claims.

The subject matter of the present invention also relates to processes for quasi-simultaneous measurement of the transmission and/or forward scattering and/or re-emission of a liquid sample and for simultaneous measurement of the transmission and forward scattering or transmission and re-emission of a liquid sample using the sensor according to the invention, driven discontinuously and continuously. Moreover, the present invention relates to the use of the sensor according to the invention for determining the color properties of painting means such as coatings and colors, pastes and pigments or the dilutions thereof.

DESCRIPTION OF THE INVENTION

"Quasi-simultaneous"

In the context of the present invention, the term "quasi-simultaneous" is intended to mean sequential registering of transmission and/or forward scattering and/or re-emission which takes place within from 1 ms to 10 s. It has been found that sequential registering of transmission and/or forward scattering and/or re-emission within from 1 ms to 10 s does not have any detrimental effects on the measurement accuracy.

"Simultaneous"

If simultaneous—i.e. synchronous—registering of transmission and forward scattering or transmission and re-emission takes place, this is preferably realized as follows:

The measurement system may be modified in such a way that only one light source (LQ) at 90° (perpendicular) is used, in order to allow simultaneous measurement of the transmission and forward scattering while omitting re-emission or allow simultaneous measurement of the transmission (180°) and re-emission while omitting forward scattering and omitting the re-emission angle from 110° to the glancing angle.

"The Sensor According to the Invention"

The sensor according to the invention is suitable for quasi-simultaneous measurement of the transmission and/or forward scattering and/or re-emission of a sample and for simultaneous measurement of the transmission and forward scattering or transmission and re-emission of a sample.

Hence, the following measurement variants are comprised by the sensor according to the invention:

Quasi-simultaneous measurement variants:
a) transmission and forward scattering
b) transmission and re-emission
c) transmission and forward scattering and re-emission
d) forward scattering and re-emission Simultaneous measurement variants:
e) transmission and forward scattering
f) transmission and re-emission Accordingly, the phrases "quasi-simultaneously" and "simultaneously" should be construed in the context of the invention in such a way that at least two of the three listed measurement types—transmission and/or forward scattering and/or re-emission—are to be carried out, with the sensor according to the invention obviously also being able to carry out individual measurements of transmission, forward scattering or re-emission. However, at least two measurements selected from transmission, forward scattering and re-emission are preferably carried out in combination quasi-simultaneously. Two measurements are always carried out in combination in the simultaneous case.

In what has preceded, and in what follows, "REM" is intended to mean re-emission, "VS" is intended to mean forward scattering and "TM" is intended to mean transmission.

In the context of the present application, "TM/VS" is intended to mean "TM" and/or "VS", i.e. transmission and/or forward scattering.

"Sample"

In the context of the present invention, a sample is intended to mean a liquid composition of individual components or a ready product mixture, in particular a colored pigment preparation. Here, the expression "colored" also includes "black" and "white" besides any colors.

Liquid compositions of individual components or ready product mixtures, in particular colored pigment preparations, are, for example, in the form of paints, coatings or pigment pastes, or as stable dilutions of paints, coatings or pigment pastes.

Stable dilutions of paints, coatings or pigment pastes are intended to mean solutions or dispersions of paints, coatings or pigment pastes, which do not segregate, flocculate or aggregate. Suitable solvents and dispersants are known to the person skilled in the art. Examples are water, organic solvents, varnishes or binders.

With the aid of the sensor according to the invention it is possible to determine transmission and/or forward scattering and/or re-emission of a liquid sample in the form of a layer quasi-simultaneously and transmission and forward scattering or transmission and re-emission of a liquid sample in the form of a layer simultaneously.

In the context of the invention, the sample in the form of a layer is a liquid pigment preparation, preferably a flowing liquid pigment preparation, or the corresponding dilution thereof, situated between two measurement windows (MF1) and (MF2), which is referred to as sample above and below.

Diluting the sample, for example for improving the flowability and optionally for adapting the measurement region, is advantageous for specific products. As a result of this, it is possible, for example, to avoid an unnecessarily high dose of expensive pigments, which may disadvantageously affect the properties of the samples.

Drawings

Below, the present invention is explained on the basis of drawings. Here, the abbreviations used in the drawings have the following meaning:
TM Transmission
REM Re-emission
VS Forward scattering
LQ Light source (REM, TM, VS)
BO Illumination optical unit (REM, TM, VS)
STS Beam splitter system
RO Reference optical unit (REM, TM, VS; REF)
DET Detector (REM, TM, VS; REF)
EO Reception optical unit (REM, TM, VS)
ST Plunger
DS(2) Sealing system plunger
P(DS2) Pump of sealing system plunger
V(DS2) Store of sealing system plunger
AK 15 Actuator (positioning system)
C-AK Controller of actuator (controller of positioning system)
POS Position measurement system
C-Pos Controller position measurement system
MZ Measurement cell
MF Measurement window
MS Measurement gap
DS(1) Sealing system of measurement cell
GP 25 Base plate
K Channel formed from the space between the measurement cell (MZ), measurement window (MF1) and advanced plunger (ST) for unimpeded passage of a liquid sample through the measurement cell (MZ)
MG Measuring device
P(P) Pump of sample
V(P) 5 Store of sample
PC(P) Sample pressure regulator FIGS. 1a to 1d represent exemplary arrangements of one or more light sources (LQ), one or more illumination optical units (BO), at least one measurement cell (MZ), at least one reception optical unit (EO) (TM/VS/REM) and at least one detector (DET) (TM/VS/REM) for measuring transmission signals generated by transmission, for measuring forward scattering signals generated by forward scattering, or for measuring re-emission signals generated by re-emission, in the sensor according to the invention.

FIG. 1a shows an exemplary arrangement of the sensor according to the invention, comprising two REM detectors (DET) (3, 4) and the reception optical units (EO) (3, 4) corresponding thereto at an angle of 25° and 45°, respectively, in relation to the glancing angle of the light source (LQ) (2) (REM), of which (DET) (3) may also be used as a transmission detector at an angle of 180° in relation to the light source (LQ) (1) (TM/VS) and (DET) (4) may be used as one of the possible forward scattering detectors at an angle of 20° to the light source (LQ) (1) (TM/VS), and the illumination optical units (BO) (1, 2) disposed downstream of the light sources (LQ) (1, 2) in the beam path. Moreover, the reference detectors (DET) (1) (REF TM/VS) and (DET) (2) (REF REM), which are preferably to be used in conjunction with the light sources (LQ) (1) (TM/VS) and (LQ) (2) (REM), including the beam splitter systems (STS) (1, 2) and reference optical units (RO) (1) (TM/VS) and (RO) (2) (REM) used in that case, are depicted.

Thus, in the exemplary arrangement of the sensor according to the invention in FIG. 1a, the light source (LQ) (REM), the illumination optical unit (BO) (REM), the at least one reception optical unit (EO) (TM/VS/REM) and the at least one detector (DET) (TM/VS/REM) are arranged on the side of the measurement window (MF1) and the light source (LQ) (TM/VS) and the illumination optical unit (BO) (TM/VS) are arranged on the side of the opposing measurement window (MF2).

FIG. 1b shows a preferred arrangement of the sensor according to the invention, comprising five REM detectors (DET) (3, 4, 5, 6, 7) and the respective reception optical units (EO) (3, 4, 5, 6, 7) at angles of 15°, 25°, 45°, 75° and 110° in relation to the glancing angle of the light source (LQ) (2) (REM), of which (DET) (3) may also be used as a transmission detector and (DET) (4, 5, 6, 7) may also be used as possible forward scattering detectors at angles of 20°, 30° and 65° in relation to the light source (LQ) (1) (TM/VS), two reference detectors (DET) (1) (TM/VS) and (DET) (2) (REM) with the respective reference optical units (RO) (1) (TM/VS) and (RO) (2) (REM), and two light sources (LQ) (1) (TM/VS) and (LQ) (2) (REM).

Thus, in the preferred arrangement of the sensor according to the invention in FIG. 1b, the light source (LQ) (2) (REM), the illumination optical unit (BO) (2) (REM), the reception optical units (EO) (3, 4, 5, 6, 7) (TM/VS/REM) and the detectors (DET) (3, 4, 5, 6, 7) (TM/VS/REM) are arranged on the side of the measurement window (MF1) and the light source (LQ) (1) (TM/VS) and the illumination optical unit (BO) (1) (TM/VS) are arranged on the side of the opposing measurement window (MF2).

FIG. 1c shows an exemplary arrangement with only one light source (LQ). The one light source (LQ) (1) (TM/REM), two REM detectors (DET) (2, 3) (REM) and the corresponding reception optical units (EO) (2, 3) thereof are arranged on the side of the measurement window (MF1), and a TM detector (DET) (1) (TM) is arranged on the measurement window (MF2) lying opposite the light source (LQ) (1) (TM/REM). If, as is preferred, use is made of a reference detector, said reference detector (DET) (4) (TM/REM) is situated together with the reference optical unit (RO) (1) and the beam splitter system (STS) (1) on the side of the measurement window (MF1).

FIG. 1d shows a further exemplary arrangement with only one light source (LQ) (1) (TM/VS), arranged on the side of the measurement window (MF2). Arranged on the side of the measurement window (MF1) are four VS detectors (DET) (4, 5, 6, 7) (VS) and the corresponding reception optical units (EO) (4, 5, 6, 7) (TM) thereof at an angle of 20°, 30°, 45° and 65° in relation to the light source LQ(1) (TM/VS) and a TM detector (DET) (3) (TM) at an angle of 180° in relation to the light source LQ(1) (TM/VS). The reference detector (DET) (1) (TM/VS) preferably to be used and the corresponding reference optical unit (RO) (1) as well as the beam splitter system (STS) (1) are arranged at the side of the measurement window (MF2).

FIG. 2a to FIG. 2d show an exemplary arrangement of a preferred embodiment of a measurement cell (MZ), in which a measurement window (MF2) is connected to a plunger (ST), the plunger (ST) being axially movable by way of actuators (AK), wherein FIGS. 2a and 2c are cut along the flow axis and FIGS. 2b and 2d are cut across the flow axis.

FIGS. 2a and 2b show two perspectives of the exemplary arrangement with an opened measurement gap (MS), i.e. an arrangement in which a plunger (ST) is withdrawn to a great extent and the separation of measurement windows (MF1) and (MF2) is at a maximum.

FIGS. 2c and 2d show two perspectives of the exemplary arrangement with a (virtually) closed measurement gap (MS); that is to say, an arrangement in which the separation of measurement windows (MF1) and (MF2) is significantly reduced by advancing a plunger (ST) into the measurement cell (MZ). It therefore represents a possible arrangement during the measurement of a sample.

Figure 2A:
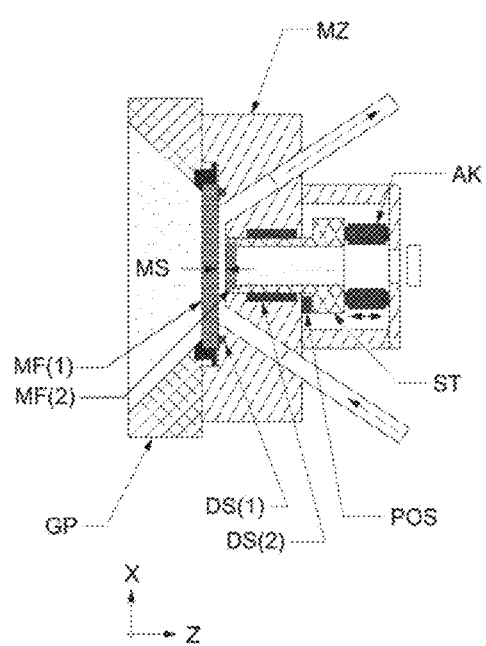

Here, FIG. 2d clearly shows that the measurement cell (MZ) is not completely closed by the advance of the plunger (ST), and hence of the measurement window (MF2), as a result of which the measurement gap (MS) is adjusted, but that the plunger (ST) projecting into the measurement cell (MZ) forms two channels (K) with the wall of the measurement cell and the measurement window (MF1), said channels forming to the left and right of the plunger (ST) in the flow direction, through which some of the sample flow guided into the measurement cell (MZ) may flow laterally around the plunger (ST) and in this manner passes through the measurement cell (MZ) in an unimpeded (and unmeasured) manner.

Figure 2B:
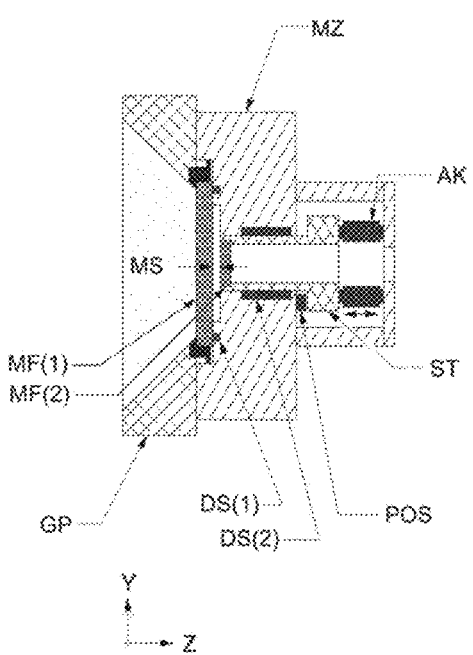
Figure 3A:
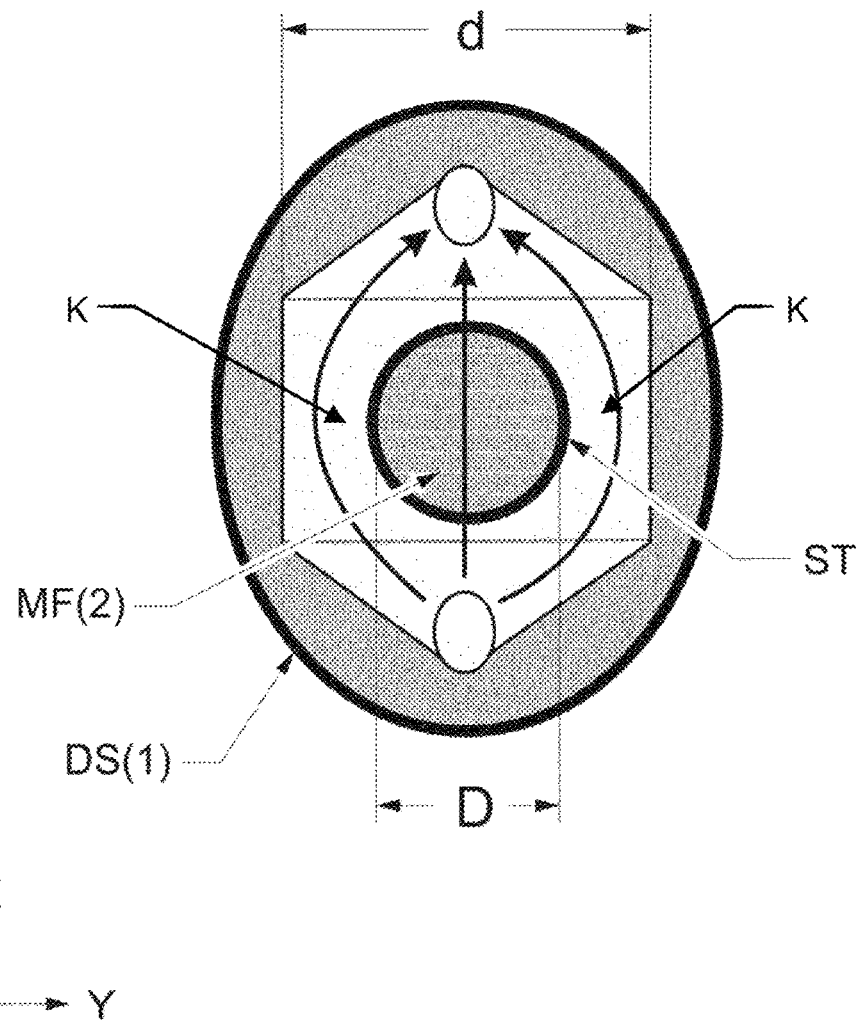
Figure 3B:
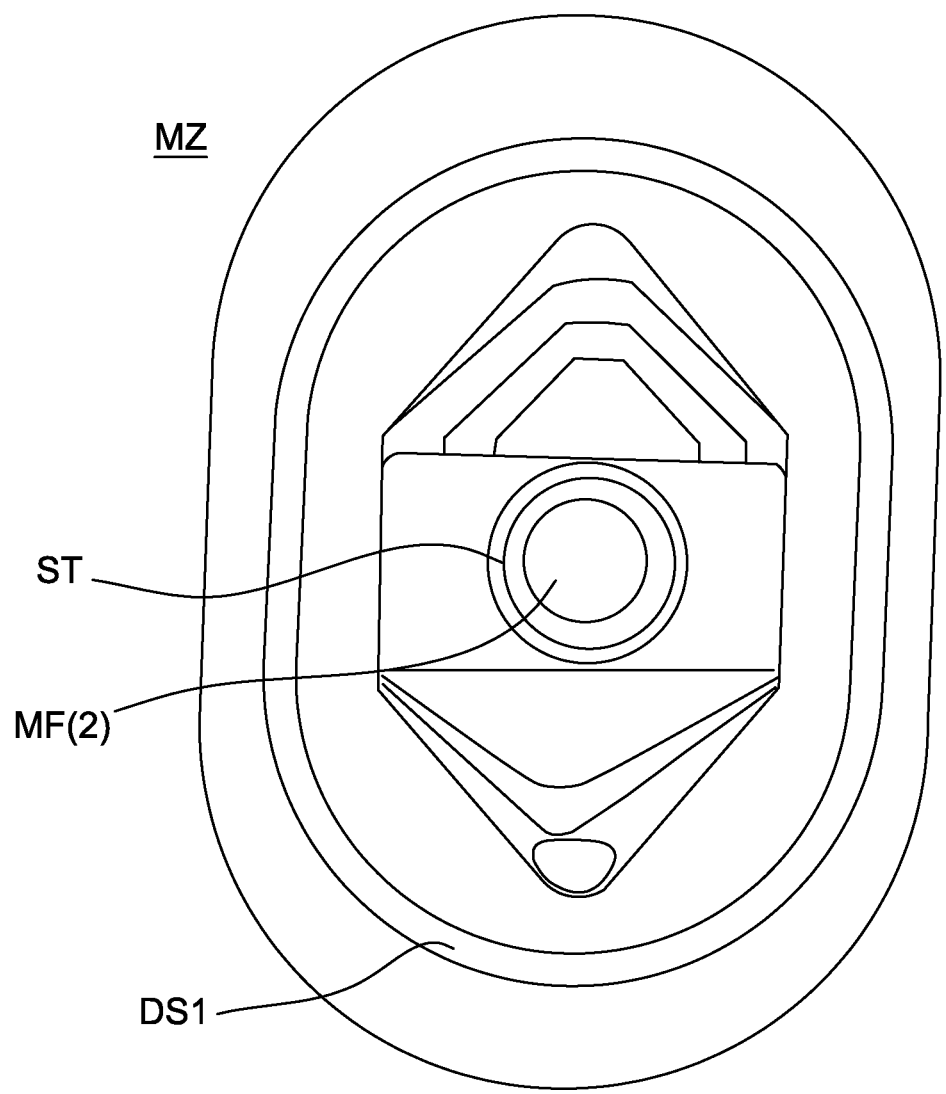

FIG. 3a shows a schematic illustration and FIG. 3b shows a photo of one side of a realized measurement cell (MZ) with a withdrawn measurement window (MF2) and plunger (ST), corresponding to the schematically depicted arrangement from FIGS. 2a and 2b, once again clarifying how some of the sample flow may flow around the plunger (ST) in an unimpeded manner by way of the channels (K) arranged to the left and right in the flow direction when said plunger is advanced and the diameter (D) of the measurement window (MF2) is less than the width (d) of the area of the measurement cell (MZ). The other part of the sample flows between the measurement windows (MF1) and (MF2) during the measurement, as depicted by the straight arrow in FIG. 3a. Shown further are the feed and discharge channels for the sample to and from the measurement cell (MZ) and a notch which, for example, together with a sealing rubber ring represents a possible embodiment of a sealing system of measurement cell (DS).

Figure 3C:
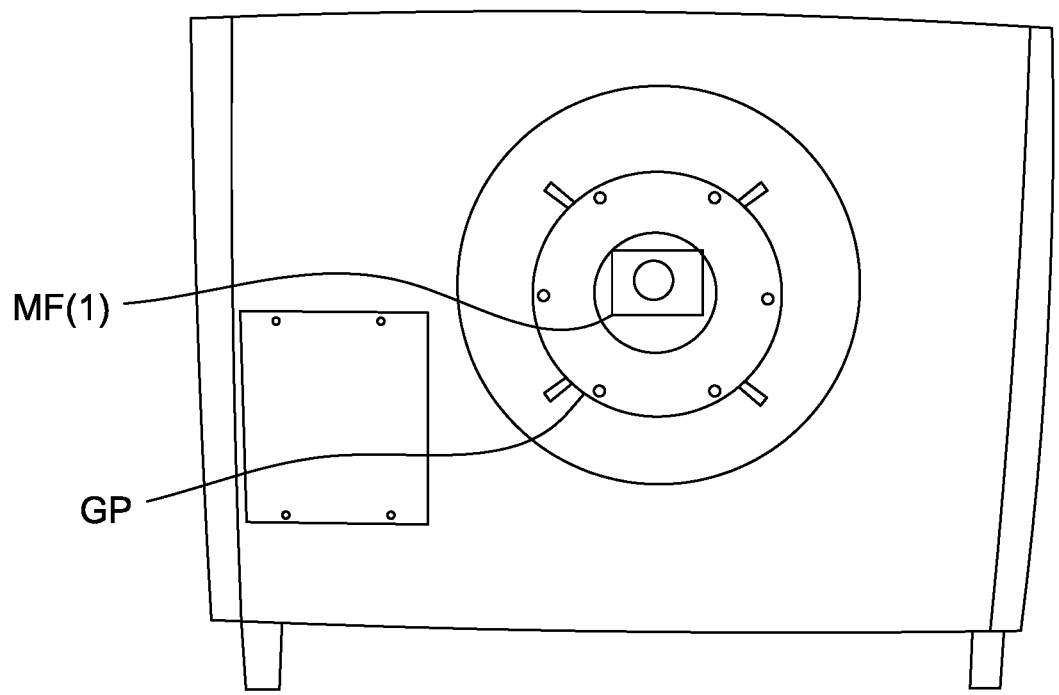

FIG. 3c shows a photo of the opposite side of the measurement cell (MZ) depicted in FIG. 3b, in which a measurement window (MF1) is assembled on a base plate (GP).

Figure 3D:
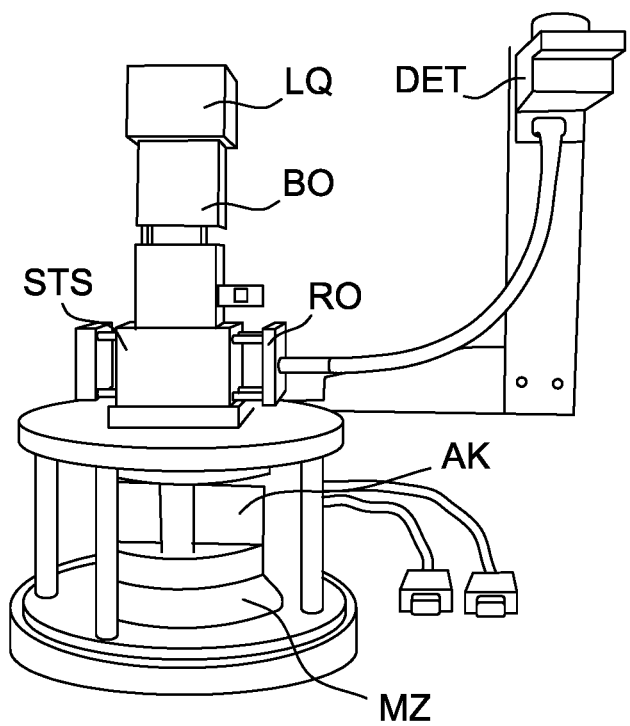

FIG. 3d shows a photo of a preferred arrangement comprising a light source (LQ), an illumination optical unit (BO), a beam splitter system (STS), a reference optical unit (RO), a detector (DET) and an actuator (AK) for driving a plunger (ST) (with a further actuator (AK), the position measurement system (POS) and the plunger (ST) being covered).

Figure 4A:
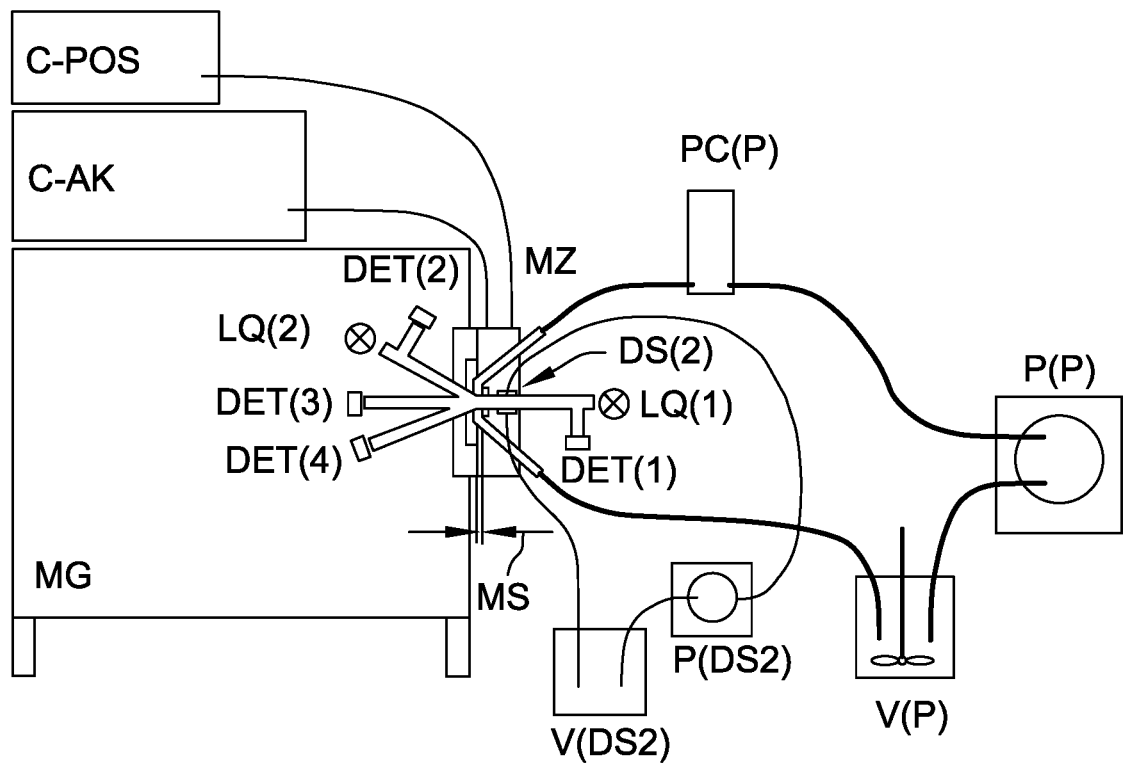
Figure 4B:
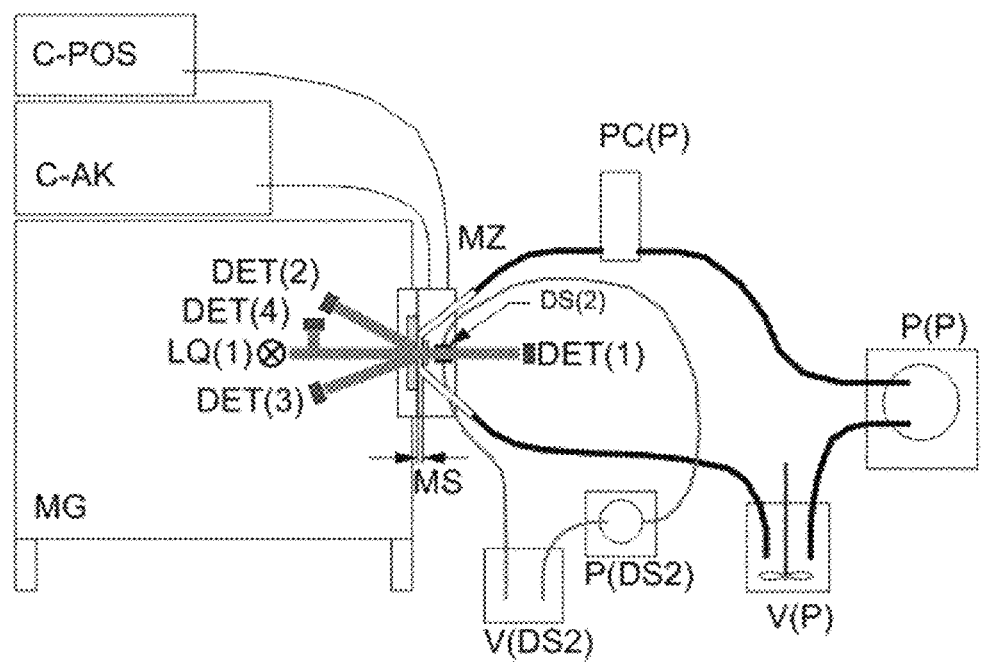

FIGS. 4a and 4b show two exemplary embodiments of an overall structure of the sensor according to the invention, comprising an exemplary embodiment of a sample supply and discharge and a sealing system of the plunger (DS2).

Figure 1A:
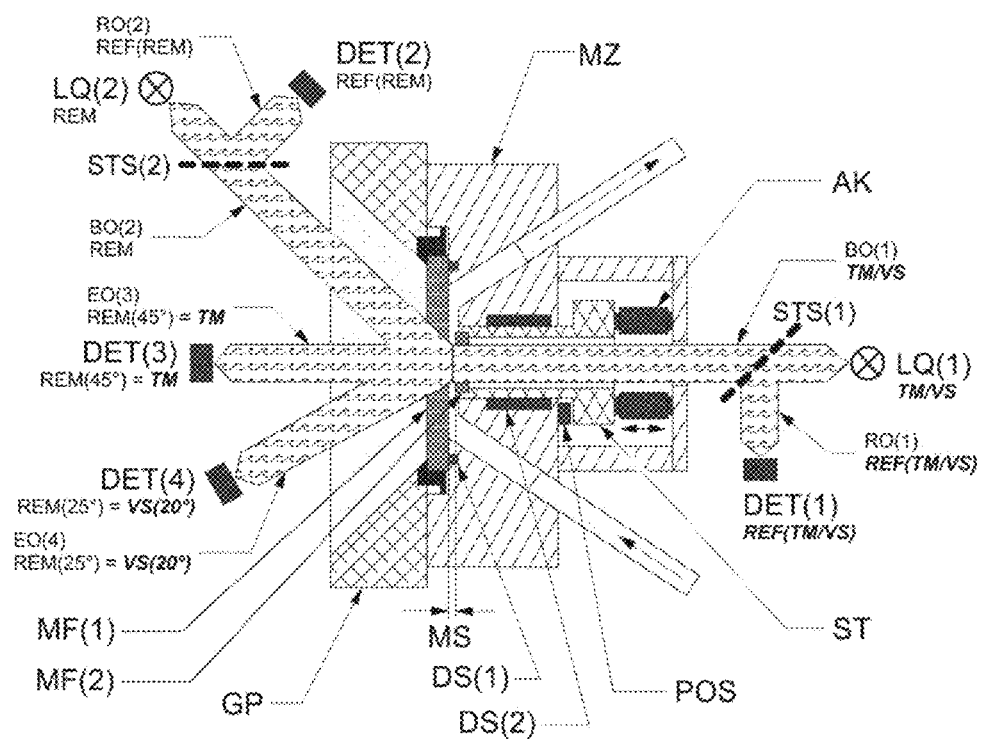
Figure 1B:
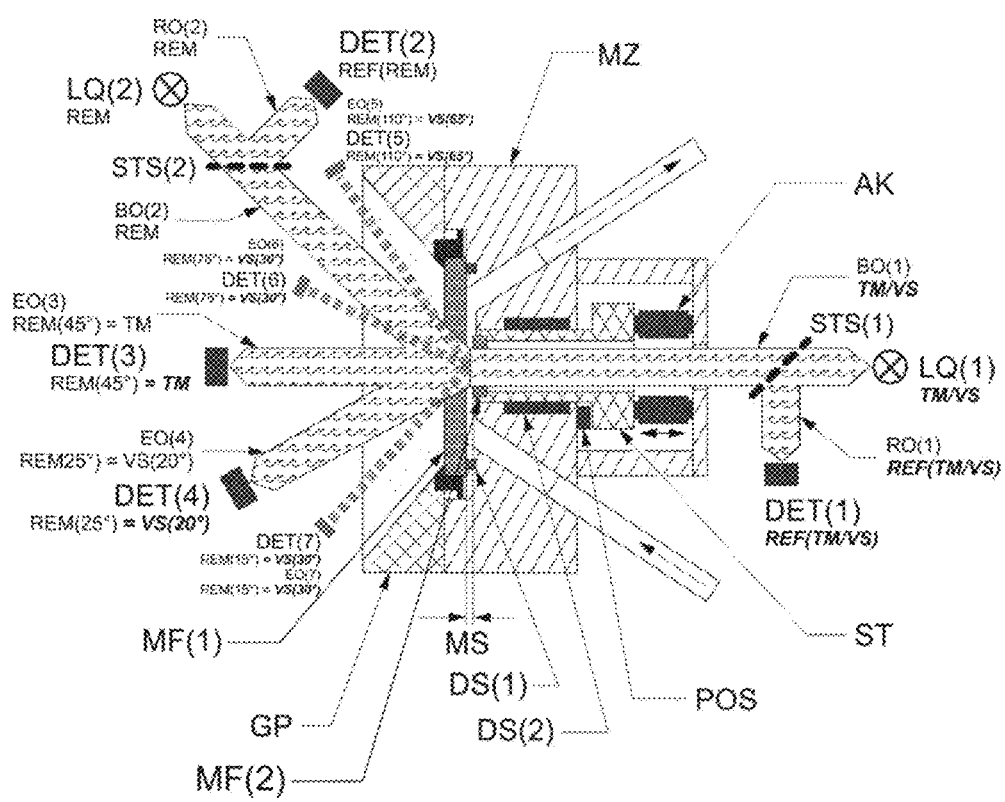
Figure 1C:
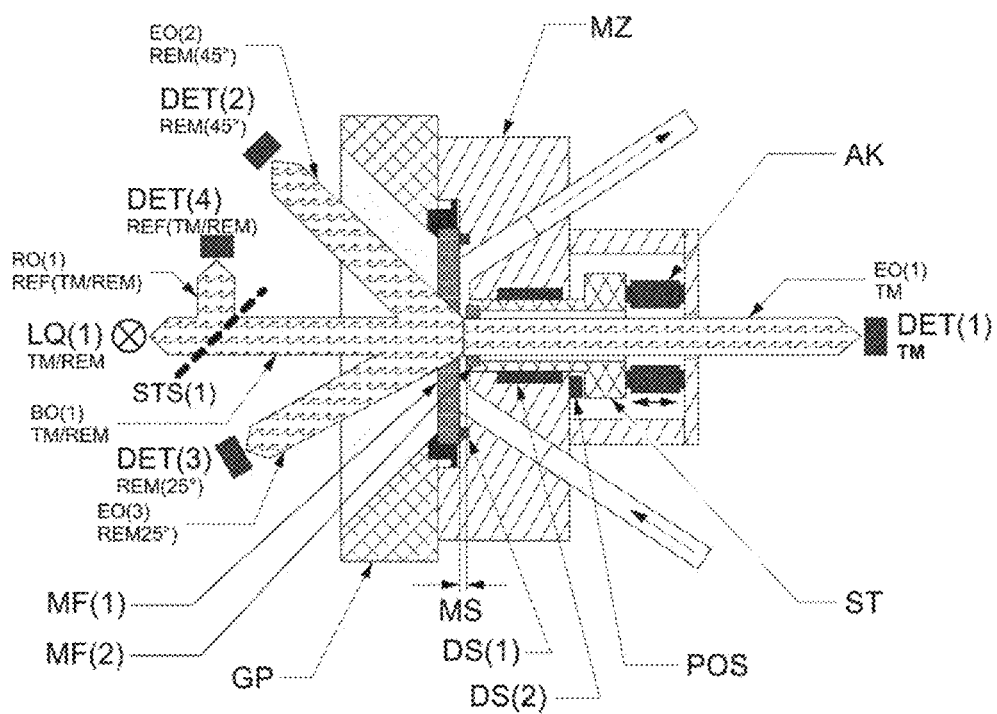
Figure 1D:
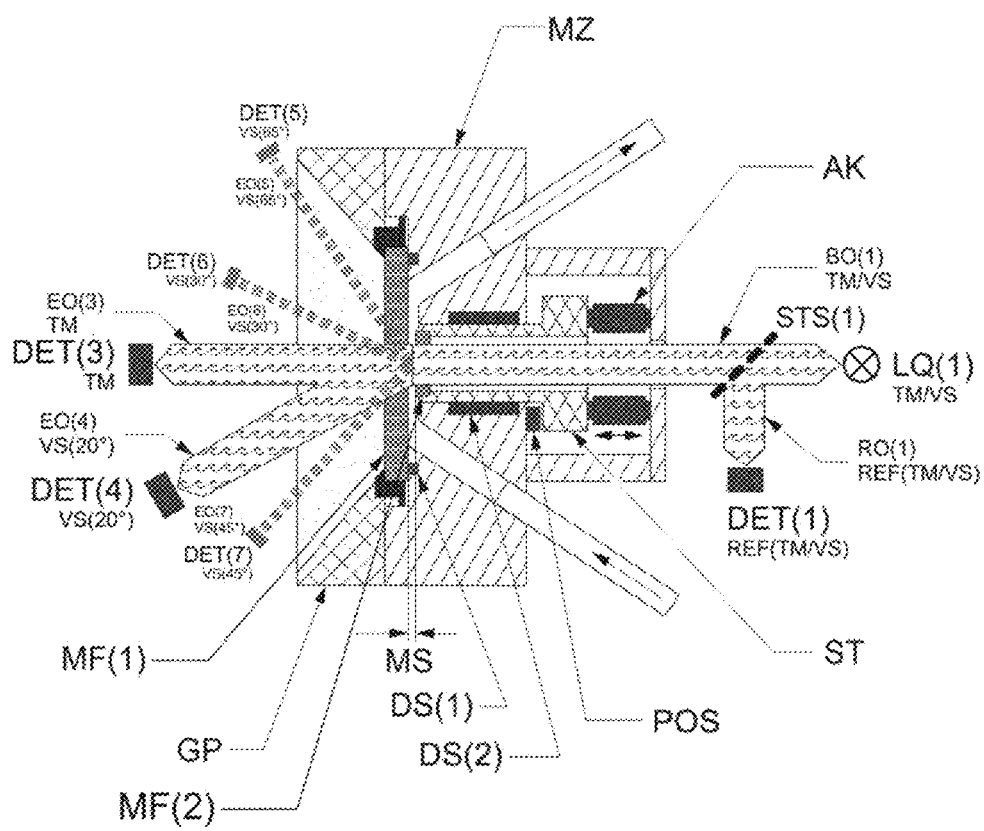

Here, FIG. 4a corresponds to the optical structure described in FIG. 1a, while FIG. 4b corresponds to the optical structure described in FIG. 1c.

Figure 5A:
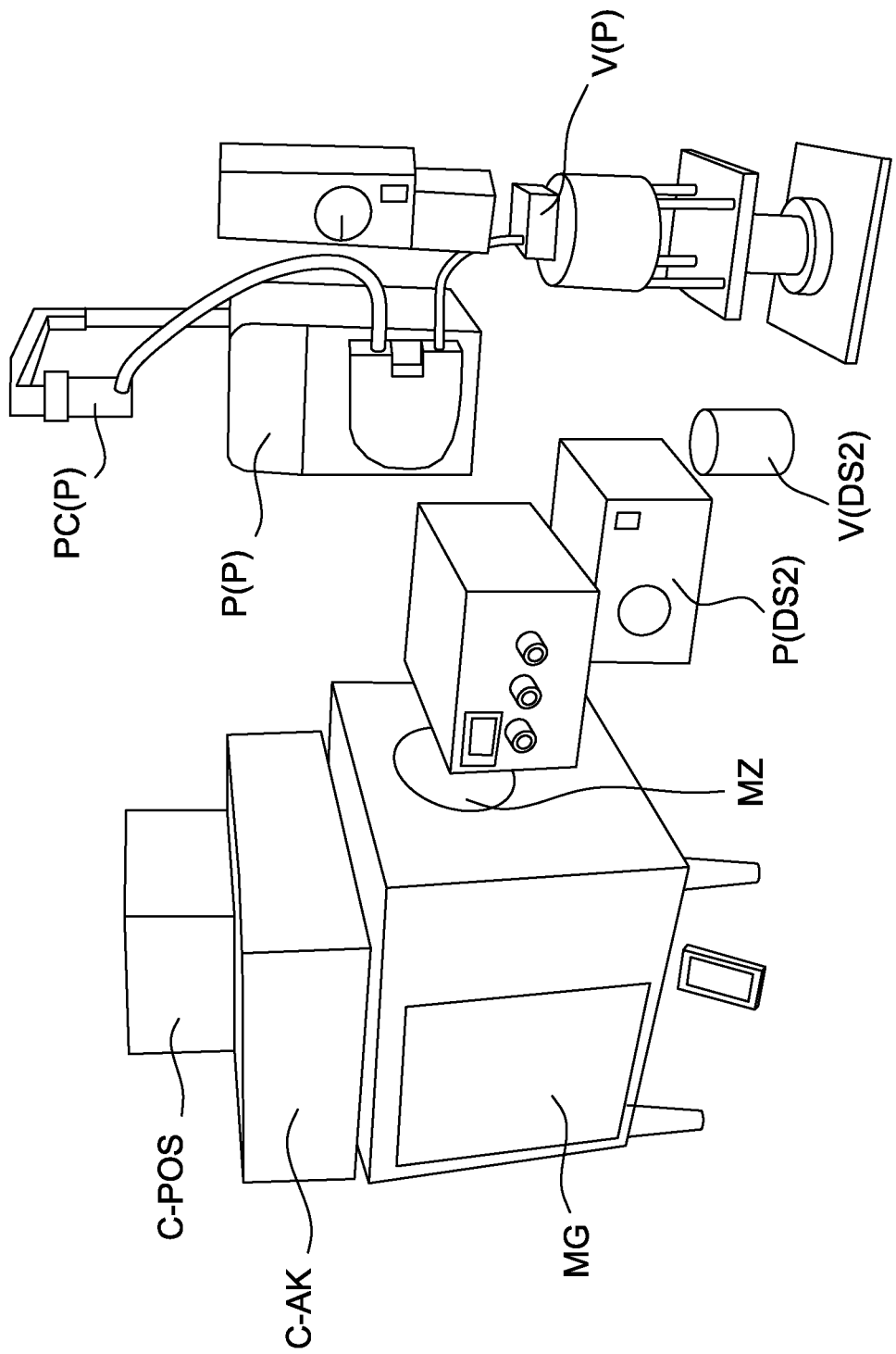
Figure 5B:
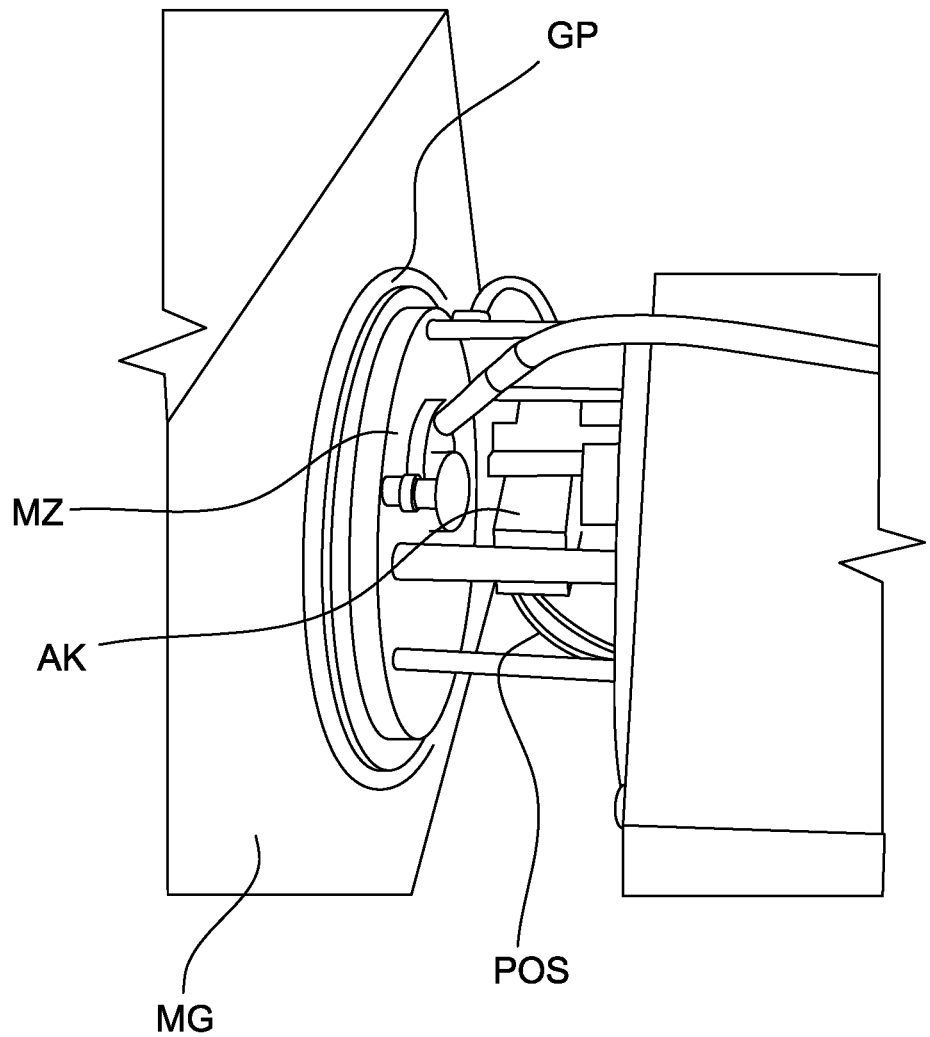

FIG. 5a and FIG. 5b show photos of a realized overall structure corresponding to the optical structure depicted in FIG. 4a.

The elements represented in the drawings and the terms used in the descriptions of the drawings, as well as suitable embodiments thereof, if not explained in more detail in the present application are known to the person skilled in the art and are elements conventionally used in process-engineering and optomechanical measurement structures.

DETAILED DESCRIPTION OF THE INVENTION

The individual components a) to e) of the sensor according to the invention will be described below:

a) one or more light sources (LQ), preferably two light sources (LQ) (TM/VS) and (LQ) (REM)

Physical Function

In principle, each individual measurement originates from a light source (LQ) which provides light in the required wavelength range with the necessary intensity, constancy and longevity.

Very many different principles may be envisioned as light sources (LQ), ranging from lamps with an incandescent filament, gas discharge lamps, to LEDs. The advantage of LEDs is the possibility of keeping the intensity constant by constant-current operation and the fact that mechanical shutters can be avoided (current off=light off). The use of lasers is also possible.

The light sources (LQ) are therefore selected, preferably independently of one another—for the case in which a plurality of light sources are used—from the group consisting of LEDs, preferably white light LEDs, RGB LEDs, arrays of LEDs with adjacent wavelength ranges; lamps with an incandescent filament; gas discharge lamps.

The light sources (LQ) generally exhibit good thermal and mechanical stability, that is to say little variation in the short-term range, no great change in the long-term range, and long lifetime. The light sources preferably exhibit a uniform spectrum, so that all wavelengths which are intended to be measured on the sample reach the detector with a sufficient intensity.

Preferably, the light sources (LQ) may be switched on and off as many times as desired, particularly preferably by means of mechanical shutters, switching of the voltage supply of the light source and/or optoelectric shutters. More particularly preferably, the light source is switched on and off by switching the voltage supply.

One preferred embodiment of the present application relates to an arrangement in which a compensation filter is arranged behind the light source. Here, "behind the light source" is intended to mean that the compensation filter is arranged following the light source in the path of the light beam from the light source. The compensation filter used in this embodiment linearizes the spectrum of the light source in such a way that the ratio between the maximum and minimum intensity of the light emitted by the light source is at most 4, preferably from 3 to 4, and not, as is conventional in the prior art, from 10 to 20. This is achieved with commercially available filter glasses.

In another preferred embodiment an IR blocking filter, a condenser and a diffuser disk are arranged behind the light source (LQ)—between the light source and the compensation filter when a compensation filter is used.

Again, "behind the light source" in the context of the present application means after the light source along the light beam. The IR blocking filter is used to reduce the heating which is exerted by the light source on the sample, the light waveguides, the compensation filter and other units of the sensor.

The condenser is used to concentrate the light from the light source onto the input of the optics, for example fiber optics. The diffuser disk is used to achieve an unstructured uniform profile of the brightness of the light from the light source over the position and the aperture angle of the light waveguides. Suitable embodiments of condensers and diffuser disks, which are suitable for the sensor according to the invention, are known to the person skilled in the art.

The shutter integrated according to the invention into the light source in one embodiment is, for example, an electromechanical shutter which can fully darken the illumination fiber. The darkening of the light source is used to measure the dark current (electrical temperature-dependent offset of the detector and of the associated amplifier electronics), which needs to be subtracted from the signal measurement value when the light source is switched on. In the form of the dark current measurement very particularly preferred here, the light source is switched off. The amount of light measured by the spectrometer is reset by the readout, but optionally (depending on the hardware) only to about 99%, so that a residue of the last measurement remains in the spectrometer and interferes with the first dark current measurement. Beyond the second successive dark current measurement, the residual value is insignificant in the scope of the measurement accuracy.

b) one or more illumination optical units (BO), preferably two illumination optical units (BO) (TM/VS) and (BO) (REM)

Physical function of the illumination optical unit (BO):

The light emitted by the light source is received in a particular solid angle range by an optical structure and guided onto the measurement object (here in general the layer of a liquid sample, for example a colored preparation). This structure is referred to as the illumination optical unit.

In addition to the illumination optical unit or units (BO), the sensor preferably comprises one or more reference optical units (RO), preferably (RO) (TM/VS) and (RO) (REM), and, in addition to the detector or detectors (DET) (TM/VS/REM), at least one detector, preferably two detectors, as reference detectors (RDET), preferably (RDET) (TM/VS) and (RDET) (REM).

Physical function of the reference optical unit (RO), reference detector (RDET):

In order to optimize the accuracy of the measurement, a part of the light emitted by the light source (LQ) may be extracted and fed to a reference detector (RDET) by a separate optical unit (the reference optical unit (RO)).

The illumination optical unit (BO) illuminates the measurement surface of the product sample with a particular solid angle. Illuminations with different main angles, 0° and 45° being known in "dry coating metrics", and with different aperture angles are possible. Parallel illumination has the aperture angle ~0°, and in likewise known "diffuse" illumination the light reaches the measurement surface from all spatial directions. This is not a case of better or worse, but good comparability of the wet measurement with the dry measurement. In the scientific literature, and in the case of some manufacturers, the use of different illumination directions is also discussed.

The illumination optical unit (BO) may in general be formed "conventionally" with lenses and apertures, but it may also contain fiber-optic elements. What is important is the consistency of the illumination intensity and the position of the illuminated spot. The amount of light provided for the reference detector (RDET) should be suitable for driving the latter in simultaneous operation with the measurement detector, and should always have a constant ratio with the illumination intensity. The reference extraction may be carried out using a fiber jointly held in parallel in the input jack in the case of fiber-optic systems, or in conventional systems using a semitransparent mirror in the beam path.

The illumination optical units (BO) independently of one another are therefore preferably configured as a fiber-optic system and/or as a conventional system with lenses and apertures.

The reference optical unit (RO), preferably reference optical units (RO) (TM/VS) and (RO) (REM), in the case of fiber-optic systems is therefore preferably formed by a fiber jointly held in parallel in an input jack, and in the case of conventional systems is preferably formed by a semitransparent mirror or similarly acting optical systems, for example a beam splitter prism or a glass plate, in the beam path.

The light waveguides are formed from glass fibers or plastic fibers or liquid light guides, as individual fibers or fiber bundles. Preferably, glass fibers having a fiber diameter of 100, 200, 400, 600, 800 μm or more, or fiber bundles, are mounted firmly, for example on the spectrometer. Particularly preferably, the fiber used as a reference guide has an adapted diameter, preferably smaller than the other light waveguides so that a representative part of the light from the light source (LQ), preferably LED, used reaches the reference detector (RDET) essentially directly and is measured as exactly as possible.

In a preferred embodiment of the sensor according to the invention, the reference guide is fed through an attenuation element, that is to say a precise spacing element with a built-in diffuser disk, in order to maintain the full aperture angle.

The comments above likewise apply for the reception optical unit (EO) mentioned under d).

c) at least one measurement cell (MZ), wherein the measurement cell (MZ) is a cell which can be flowed through and which comprises two opposing measurement windows (MF1) and (MF2) arranged parallel, which are arranged with respect to one another in such a way that a measurement gap (MS), which is filled with the sample to be measured, is formed between the measurement windows (MF1) and (MF2), the measurement windows (MF1) and (MF2) having a defined separation from one another which is variably adjustable Physical Function:

The layer to be measured is formed by a liquid sample, which generally fills the gap (measurement gap (MS)) formed by two opposing measurement windows (MF1) and (MF2) arranged in parallel. The sample is preferably a flowing sample, the flow path being the measurement gap (MS) formed by the two opposing measurement windows (MF1) and (MF2) arranged in parallel.

The measurement cell (MZ) is a cell which can be flowed through and which provides two opposing measurement windows (MF1) and (MF2) (for re-emission, transmission and forward scattering) at a fixed or variable, but always precisely measured, separation from one another, between which the sample, preferably the flowing sample, is located.

For transporting the sample to be tested into a measurement gap (MS), the latter is opened, that is to say the separation of the two measurement windows (MF1) and (MF2) is increased until the layer has, in general, been completely renewed. Thereupon, for the actual measurement, the measurement gap (MS) between the measurement windows (MF1) and (MF2) is narrowed (again) to the desired measurement position or the separation of the two measurement windows (MF1) and (MF2) is reduced, with the excess sample being able to escape, preferably in an unimpeded manner, by way of the channels (K). In general, the remaining sample still is slightly sheared, which is conducive to the measurement.

The defined separation of the measurement windows (MF1) and (MF2) is variably adjustable, preferably in flow-through operation, that is to say the measurement gap (MS) and hence also the layer thickness of the sample, preferably of the flowing sample, formed by the defined separation of the opposing measurement windows (MF1) and (MF2) arranged in parallel, may be varied, preferably varied in flow-through operation, with the adjusted defined separation always being determinable precisely. A variably adjustable but always precisely determinable separation, preferably in flow-through operation, may be required to adapt the measurement gap (MS) or the layer thickness individually, preferably continuously, to the respective sample in order thus to adjust a layer thickness, depending on requirements, in which the sample is covering, semi-transparent or transparent.

The defined separation of the measurement windows (MF1) and (MF2) is preferably from 1 to 10 000 μm, particularly preferably from 5 to 5000 μm, more particularly preferably from 10 to 500 μm.

Preferably, the measurement windows (MF1) and (MF2) are respectively plane plates formed independently of one another from material which is transparent for the wavelength range used, with sufficient mechanical and chemical stability, for example plastic(s) (for example PS, PC, PET, PMMA), glass (for example BK7, BaK2, LaSF9, borosilicate glass, quartz glass), quartz, zirconia, semiprecious stone (for example zircon), or precious stone (for example topaz, sapphire, diamond).

Preferably, the measurement window (MF1) has a thickness of from 1 to 12 mm, particularly preferably from 4 to 10 mm, more particularly preferably from 6 to 8 mm. The measurement window (MF1) generally has a diameter of from 10 to 100 mm, preferably from 30 to 70 mm.

Preferably, the measurement window (MF2) has a thickness of from 1 to 12 mm, particularly preferably from 1 to 8 mm, more particularly preferably from 1 to 4 mm. The measurement window (MF2) generally has a diameter (D) of from 5 to 100 mm, preferably from 10 to 30 mm.

In a preferred embodiment, the defined separation between the measurement windows (MF1) and (MF2) in through-flow operation is variably adjustable, i.e. the flowing sample need not be stopped, interrupted, reduced or adapted in any other way to adapt the defined separation between the opposing measurement windows (MF1) and (MF2) arranged in parallel, adjust said separation to the desired magnitude and determine the exact position.

In a further preferred embodiment of the sensor according to the invention, one of the two measurement windows (MF1) or (MF2), preferably (MF2), is connected to a plunger (ST), preferably an axially movable plunger (ST), which permits an individual adjustment, preferably a continuous individual adjustment, of the separation between the two mutually opposing measurement windows (MF1) and (MF2) arranged in parallel. In any case, the separation between the two mutually opposing measurement windows (MF1) and (MF2) arranged in parallel may be increased or reduced by moving the plunger (ST), preferably by axially moving the plunger (ST), as a result of which the measurement gap (MS) and hence also the layer thickness of the sample, preferably flowing sample, to be measured may be adapted individually, preferably continuously.

In a particularly preferred embodiment of the sensor according to the invention, one of the two measurement windows (MF1) or (MF2), preferably (MF2), is connected to a movable plunger (ST), preferably an axially movable plunger (ST), which permits an individual adjustment, preferably a continuous individual adjustment, of the separation between the two mutually opposing measurement windows (MF1) and (MF2) arranged in parallel, wherein the diameter (D) of the measurement window (MF1) or (MF2), preferably (MF2), connected to the plunger is less than the width (d) of the area of the measurement cell (MZ) (cf. FIGS. 2a-d and 3a), on which the measurement window (MF1) or (MF2), preferably (MF2), connected to the plunger rests. As a result of the diameter (D) of the measurement window (and consequently of the plunger (ST)) being less than the width (d) of the area of the measurement cell (MZ), the sample channel is not completely closed when driving together the measurement windows (MF1) and (MF2), i.e. when reducing the measurement gap (MS), during which the plunger (ST) is advanced into the measurement cell; two channels (K) are formed laterally in relation to the plunger (ST) (to the left and right in the flow direction). The advantage emerging herefrom is the unimpeded escape of the excess sample in the channels (K) via the sides of the measurement window when reducing the separation between the measurement windows (MF1) and (MF2). A further advantage of this preferred arrangement of the measurement cell (MZ) is that some of the sample introduced into the measurement cell, preferably some of the flowing sample introduced into the measurement cell, may flow around the plunger (ST) in an unimpeded manner by way of the channels (K), said plunger protruding into the measurement cell when reducing the measurement gap (MS), as a result of which this unmeasured part of the sample (the sample has not passed through the measurement gap (MS) between the measurement windows (MF1) and (MF2)), preferably the unmeasured part of the flowing sample, may pass through the measurement cell (MZ) virtually unimpeded (cf. FIGS. 2a-2d and 3a-b). Such an embodiment is suitable, predominantly for continuous measurement operation or continuous sample supply, by virtue of the measurement gap only being reduced when required, without significantly reducing the through-flow through the measurement cell (MZ) itself. Hence, the supply of the sample, preferably the flowing sample, need not be reduced, stopped or interrupted in any other way during continuous measurement operation.

The position of a plunger (ST), and hence also the separation of the two measurement windows (MF1) and (MF2), may generally be adjusted by a positioning system, preferably by one or more actuators (AK) with corresponding controller (C-AK), wherein the precisely reached position may be determined by a position measurement system (POS) and a corresponding controller (C-POS). Exemplary arrangements are depicted in FIGS. 1a to 1d and FIGS. 2a to 2d.

In the sensor according to the invention, a measurement gap (MS), that is to say the defined separation of the measurement windows (MF1) and (MF2), is preferably variably adjustable with an accuracy of, on average, 40 to 100 nm, particularly preferably of, on average, 40 to 60 nm (standard deviation of the difference between the actual value and intended value), preferably in through-flow operation.

In a particularly preferred embodiment of the sensor according to the invention, one of the two measurement windows (MF1) or (MF2), preferably measurement window (MF2), is connected to a plunger (ST), preferably an axially movable plunger (ST), wherein the position of the plunger (ST), and hence also the separation of the two measurement windows (MF1) and (MF2), are variably adjusted by a positioning system, preferably by one or more actuators (AK) with a corresponding controller (C-AK), with an accuracy of, on average, 40 to 100 nm, particularly preferably of, on average, 40 to 60 nm (standard deviation of the difference between the actual value and intended value), preferably in through-flow operation, wherein the precisely reached position may preferably be determined by a position measurement system (POS) and a corresponding controller (C-POS). Exemplary arrangements are depicted in FIGS. 1a to 1d and FIGS. 2a to 2d.

For the case in which the sample to be measured flows through a measurement gap (MS), shearing of the sample takes place during passage through the gap. The shearing is preferably achieved by the pressure drop in the gap preferably being from 0.1 to 3 bar over a length of from 1 to 30 mm, particularly preferably from 0.5 to 1.5 bar over a length of from 2 to 15 mm.

In order to maintain a defined sample state and therefore achieve comparable measurement data—in the case in which the sample to be measured flows through a measurement gap (MS)—constant shearing of the sample is preferred. This is preferably done by continuous monitoring of the input pressure, that is to say the pressure at the input point of the liquid pigment preparation in the measurement gap (MS).

Pressure monitoring is preferred in order to allow defined shearing at the measurement position. If this is ensured by other measures (for example known pump power, viscosity and gap width), pressure measurement may be omitted. A plurality of variants may be envisioned for a pressure measurement, namely the T configuration, the V configuration, measurement by a pressure transducer flowed through, as well as a bore in the product cell. The structure of the aforementioned configurations is known to the person skilled in the art. Selection criteria are sufficiently accurate measurement of the relatively low pressures, insensitivity to pressure variations (for example when the product is delivered by a pulsing pump), and easy flushability (no dead spaces) or at least cleanability.

The adjustment of the input pressure is, inter alia, dependent on the hiding power and on the viscosity of the sample, in particular of the liquid pigment preparation or dilution thereof. If, for example, a coating which does not cover strongly is used as a sample, it is necessary to choose a measurement cell (MZ) with a larger measurement gap (MS) than when a more strongly covering coating is used. The volume flow rate must then be readjusted so that the pressure drop remains constant.

d) at least one reception optical unit (EO) (TM/VS/RENT)

Physical Function:

The light emitted by the sample is received in a solid angle range by the reception optical unit (EO) and delivered to the detector (DET). Depending on the side on which this solid angle range lies, re-emission (same side as (LQ) in relation to the measurement window) or transmission/forward scattering (the light having passed through the sample to the other side of the light source (LQ) in relation to the measurement window is registered) is referred to.

The reception optical unit (EO) is in principle constructed in a similar way to the illumination optical unit (BO) (see the explanations relating to the illumination optical unit (BO), section b)). In one embodiment, it is possible to carry out angle-resolved measurement of the light emitted by the sample so that a plurality of reception optical units, registering only a particular solid angle range, are arranged with a respective detector concentrically next to one another and are operated sequentially, or preferably in parallel.

Preferably, the reception optical units (EO) are configured independently of one another as a fiber-optic system and/or as a conventional system with lenses and apertures.

Conventionally, the sensor according to the invention contains 1, 2, 3, 4, 5, 6, 7 or 8 reception optical units (EO).

e) at least one detector (DET) (TM/VS/REM for measuring transmission signals generated by transmission, for measuring forward scattering signals generated by forward scattering and for measuring re-emission signals generated by re-emission Physical Function:

The light collected by the reception optical unit (EO) reaches the detector (DET), which analyzes the spectrum of the light—generally in comparison with the spectrum of the light source. This is usually done by a wavelength-resolved measurement of the intensity with a spectrometer.

The detector (DET) is the complementary counterpart of the light source (LQ). The spectral property of the sample is determined by comparison of the illuminating spectrum (preferably from the measurement of the reference channel) with the spectrum emitted by the sample. The result is always an intensity ratio in a wavelength range, or a series of measurement values (array) for each of the wavelength ranges determined.

In principle, it is equivalent whether the wavelength selection is already carried out on the light-source side (tunable light source, or wavelength-selective element in the beam path), combined with a broadband detector with one channel, or on the detector side, for example with a so-called monolithic spectrometer (glass block with dispersion grating and linear CCD or diode array). The latter embodiment requires no moving parts, and is fast and robust.

Preferably, the detectors (DET) are therefore intensity detectors, particularly preferably spectrally resolved intensity detectors, more particularly preferably fiber-optic monolithic linear diode array sensors.

Readout of the receivers and digitization of the signals with a good resolution (for example 15 bits) are commercially available, and the signal/noise ratio can generally be improved by measurement repetition and averaging.

Conventionally, the sensor according to the invention contains 1, 2, 3, 4, 5, 6, 7 or 8 detectors.

In a preferred arrangement of the sensor according to the invention, at least 3 detectors (DET), preferably 5 detectors (DET), are arranged for multi-angle measurement of re-emission signals generated by re-emission at at least 3 solid angles, preferably 5 solid angles, in the solid angle range of 10° to 115°, preferably 15°, 25°, 45°, 75° and 110°, in relation to the glancing angle of the light source (LQ) (REM).

In a further preferred arrangement of the sensor according to the invention, at least 2 detectors (DET), preferably at least 3 detectors (DET), are arranged for multi-angle measurement of forward scattering signals generated by forward scattering at at least 2 solid angles, preferably at least 3 solid angles, in the solid angle range of >0° to <90°, preferably in the solid angle range of 10° to 80°, particularly preferably 20°, 30°, 45° and 65°, in relation to the light source (LQ) (VS).

In a particularly preferred arrangement of the sensor according to the invention, at least 3 detectors (DET), preferably 5 detectors (DET), are arranged for multi-angle measurement of re-emission signals generated by re-emission at at least 3 solid angles, preferably 5 solid angles, in the solid angle range of 10° to 115°, preferably 15°, 25°, 45°, 75° and 110°, in relation to the glancing angle of the light source (LQ) (REM), wherein these detectors are likewise used for multi-angle detection of forward scattering signals generated by forward scattering at at least 2 solid angles, preferably at least 3 solid angles, in the solid angle range of >0° to <90°, preferably in the solid angle range of 10° to 80°, particularly preferably 20°, 30°, 45° and 65°, in relation to the light source (LQ) (VS).

Here, there is a certain tolerance when registering a solid angle, that is to say it is possible not to register a sharply delimited solid angle but rather a solid angle range which, depending on the solid angle, may have different sizes. By way of example, in the case of REM measurements, tolerances of up to ±8° are permitted at solid angles of 15°, 25° and 45° and tolerances of up to ±10° are permitted at a solid angle of 75° and tolerances of up to ±20° are permitted at a solid angle of 110°, in each case in relation to the glancing angle of the light source (ASTM E2194).

A multi-angle measurement of the forward scattering, in particular of the white light scattering, allows a comprehensive characterization of angle-dependent particles, in particular of effect pigments or effect pigment preparations, by determining the dimensions and isotropy of the particles and registering the angle-dependent color loci.

As already mentioned under b), in addition to the illumination optical unit or units (BO) the sensor preferably comprises one or more illumination optical units, preferably two illumination optical units as reference optical units (RO), preferably (RO) (TM/VS) and (RO) (REM), and in addition to the detector or detectors (DET) (TM/REM/VS) at least one detector, preferably two detectors, as reference detectors (RDET), preferably (RDET) (TM/VS) and (RDET) (REM).

In a preferred embodiment of the sensor according to the invention, a plurality of light sources (LQ) and a plurality of illumination optical units (BO) are present, wherein a light source (LQ) (REM), an illumination optical unit (BO) (REM), at least one reception optical unit (EO) (TM/VS/REM) and at least one detector (DET) (TM/VS/REM) are arranged on the side of the measurement window (MF1) and a light source (LQ) (TM/VS) and an illumination optical unit (EO) (TM/VS) are arranged on the side of the opposing measurement window (MF2).

In a further preferred embodiment of the sensor according to the invention, only one light source (LQ) and only one illumination optical unit (BO) are present, which are arranged either on the side of the measurement window (MF1) or on the side of the measurement window (MF2), wherein preferably at least one reception optical unit (EO) (TM/VS) and at least one detector (DET) (TM/VS) for measurement of the transmission and/or forward scattering are arranged on the measurement window (MF2) or (MF1) opposing the one light source (LQ) and one illumination optical unit (BO) in each case, and preferably at least one reception optical unit (EO) (REM) and at least one detector (DET) (REM) for measurement of the re-emission are arranged on the side of the measurement window (MF1) or (MF2) which corresponds to the side of the one light source (LQ).

In a particularly preferred embodiment of the sensor according to the invention, all the units (a) to (e) of the sensor are accommodated in a common or two-part housing. The housing is preferably a mobile housing, which can be transported without difficulty to the place of use, for example a housing on rollers. The housing is preferably thermally regulated, since a constant temperature leads to an improvement of the measurement accuracy (ventilation, thermostatically regulated thermal dissipation, cooling water, coolers/fans, and/or thermostated measurement environment). Irrespective thereof, it may also be necessary to comply with certain tolerances for the sample temperature, since significant evaporation of the solvents, thermal sensitivity and thermochromatic effects are possible (ventilation, thermostatically regulated thermal dissipation, cooling water, coolers/fans, and/or thermostated measurement environment). At the same time, this avoids cycling heating which may lead to mechanical variations.

Furthermore, contact with the light waveguides as well as the other elements of the sensor is avoided by the housing, and air sealing is ensured. By the common housing, therefore, an increase in the measurement accuracy of the sensor is achieved.

In a further preferred embodiment, the sensor according to the invention contains a sealing system (DS(2)), as depicted in the drawings, said sensor in general facilitating precise adjustment of the plunger (ST) with the available forces when fine particular pigments, polymers and solvents are present. The sealing systems known to a person skilled in the art should be selected and used according to these considerations.

Accuracy

For reliably registering spectrometric measurement data for ascertaining the color properties, such as color locus, hiding power and color strength, or absorption (K or A) and scattering (S), of liquid samples, it is particularly important to precisely adjust or know the spacing of the measurement windows (MF1) and (MF2) (that is to say the measurement gap (MS) and hence the layer thickness). Preferably, the desired measurement gap (MS) (intended value) is adjusted with an accuracy (standard deviation between actual value and intended value) of, on average, 40 to 100 nm, particularly preferably of, on average, 40 to 60 nm.

One-Step Driving

In the case of one-step driving, only one layer thickness is set, the absolute knowledge of which must be determined as accurately as possible for ascertaining the color properties of a sample.

Two-Step Driving

Absolute knowledge of the layer thickness is not mandatory if it is possible to carry out two measurements with a known difference in the layer thickness and the difference in the transmission (hence absorption, known to a person skilled in the art, is also accessible to him) is then related to this layer thickness difference. This procedure renders it possible to determine the same product properties as in the "one-step measurement". The two-step measurement significantly facilitates the measurement in practice, however, since the technically available absolute accuracy of piezo drives, which are preferably used as actuators (AK), is very high, while the reproducibility of a measurement gap (MS), that is to say the layer thickness, after dismantling and assembly, for example after cleaning the measurement cell in the open state, is normally inferior by an order of magnitude. Thus, when the layer thickness is referred to below, this always involves the possibility of carrying out and evaluating two measurements with a known layer thickness difference.

Determining the Ideal Layer Thickness

For completely characterizing the sample, it is necessary to set one or more suitable layer thicknesses, wherein the layer thickness ideal for the measurement also depends on the sample itself. Pursuant to Kubelka-Munk theory, a covering layer and non-covering layer may be set for REM measurements and a sufficient signal strength being present is important for the TM and VS measurement. By way of example, for the purposes of measuring the forward scattering, this means that the measurement effect, i.e. the change of the measurement signal depending on the interaction with the sample, is too low in order to be able to determine the properties of the sample of a product with sufficient precision in the case of a layer thickness that is too small. On the other hand, if the layer thickness is selected to be too thick, so little light penetrates through the layer that this light amount cannot be measured with the necessary precision. Thus, it may be necessary to set different layer thicknesses for all three measurement types, that is to say for re-emission, forward scattering and transmission, in order to obtain the desired significant measurement effect.

The sensor according to the invention is distinguished by a highly accurate optical geometry for quasi-simultaneous measurement of the transmission and/or forward scattering and/or re-emission and for simultaneous measurement of the transmission and forward scattering or transmission and re-emission, and by a highly precise system for adjusting a measurement gap (MS), wherein, preferably, one of the two measurement windows (MF1) or (MF2), preferably (MF2), is connected to a movable plunger (ST), preferably an axially movable plunger (ST), which permits an individual adjustment, preferably a continuous individual adjustment, of the separation between the two mutually opposing measurement windows (MF1) and (MF2) arranged in parallel. The light source (LQ) or the light sources (LQ) are preferably referenced by way of a reference detector (RDET). In any case, the separation between the two mutually opposing measurement windows (MF1) and (MF2) arranged in parallel may be increased and reduced by moving the plunger (ST), preferably by axially moving the plunger (ST), as a result of which the measurement gap (MS) and hence also the layer thickness of the sample, preferably of the flowing sample, may be adapted individually, preferably continuously. Clearly, the measurement window (MF1) or (MF), preferably (MF2), connected to the plunger (ST) is connected to the plunger (ST) in a way which does not lead to an interruption of the light beam through the sample.

The usually preferred layer thicknesses, to be adjusted by way of the measurement gap (MS), generally lie in the range of non-covering layers (e.g. 10-50 µm) to covering layers (e.g. 500-700 µm) for the re-emission measurement and in the range of semi-transparent layers (10-300 µm) for the transmission measurement and forward scattering measurement. Accuracy is a challenge, particularly in the case of the transmission measurement, since the error of the layer thickness directly influences the concentration of the pigments set therewith, that is to say 1 µm uncertainty in the case of e.g. a measurement gap of 10 µm means +/−10% uncertainty when determining the pigment concentration. It was found that suitable measurement results are obtained by the sensor according to the invention in the case of a defined separation of the measurement windows (MF1) and (MF2) of preferably 1 to 10 000 µm, particularly preferably 5 to 5000 µm, very particularly preferably 10 to 500 µm.

The preferred referencing of the re-emission, transmission and forward scattering measurement is generally carried out by simultaneously spectrally registering both the sample signal and the light-source signal during the measurement, so that variations of the light source can be registered and can be calculated out from the sample signals and the re-emission, transmission and forward scattering can thereby be determined independently of the illumination.

With the aid of the sensor according to the invention, it was possible to achieve very high absolute measurement accuracies, in general of from <0.5 to 0.05ΔE, which is achieved by an absolute measurement accuracy of from <0.1% to 0.01% of the raw measurement data (re-emission, transmission and forward scattering intensities). Here, ΔE is the term, known to a person skilled in the art, from the L*a*b* color space (CIELAB, EN ISO 11664-4) which specifies the Euclidean color distance of the L*a*b* values of two color loci.

Before the start of the measurements, the sensor is preferably calibrated. This may in principle be done in any way known to the person skilled in the art. One choice of suitable calibration routines is mentioned below:

Calibration Routines a. Distance Positioning System

Calibration may be carried out by means of absorbing (colored) solutions by setting various measurement gaps (MS), measuring the associated transmission and carrying out an evaluation according to the Lambert-Beer law known to a person skilled in the art, in which the attenuation of the intensity of radiation when passing through a medium with an absorbing substance is described dependent on the concentration of the absorbing substance and the layer thickness. High accuracies in the calibration of the positioning system are obtained, in particular, in the linear range of the Lambert-Beer law.

b. Re-Emission

Calibration may be carried out by means of a white standard in a solid or liquid form. The air gap between the measurement window (MF1) or (MF2), relevant for the re-emission measurement, and a solid white standard is preferably filled with immersion fluid, for example immersion oil.

c. Transmission

Calibration may be carried out with a clear nonabsorbing or absorbing solution at different measurement gaps (MS).

d. Forward Scattering

Calibration of the forward scattering is possible with liquid scattering standards (for example latex dispersions, $TiO_2$ dispersions, but also emulsions or other scattering standards) in one or more measurement gaps (MS).

Process

In a further embodiment, the present invention relates to a process for quasi-simultaneous measurement of the transmission and/or forward scattering and/or re-emission of a sample and for simultaneous measurement of the transmission and forward scattering, or transmission and re-emission, of a sample.

The measurement operation (measurement process) with the aid of the sensor according to the invention preferably takes place by carrying out the following steps i) to viii) and repetitions as often as desired, the respective steps being carried out according to the desired process variant, the following process variants being included:

Quasi-Simultaneous Measurement Variants:
a) Transmission and forward scattering
b) Transmission and re-emission
c) Transmission and forward scattering and re-emission
d) Forward scattering and re-emission Simultaneous Measurement Variants:
e) Transmission and forward scattering
f) Transmission and re-emission Process steps:
i) adjusting measurement gap (MS) with a defined separation X of the measurement windows (MF1) and (MF2)

ii) measuring transmission (TM) in process variants a), b) and c), iii) measuring forward scattering (VS) in process variants a), c) and d), iv) measuring re-emission (REM) in process variants b), c) and d), v) adjusting a new measurement gap (MS), deviating from step i), with a defined separation Y of the measurement windows (MF1) and (MF2), vi) measuring transmission (TM) in process variants a), b) and c), vii) measuring forward scattering (VS) in process variants a), c) and d), viii) measuring re-emission (REM) in process variants b), c) and d), wherein the individual steps i) to viii) may be repeated as often as desired and wherein the defined separations of X and Y are, independently of one another, 1 to 10 000 μm, preferably 5 to 5000 μm, particularly preferably 10 to 500 μm, where X≠Y.

In the quasi-simultaneous measurement variant, steps ii) to iv) and vi) to viii), occurring after "adjusting measurement gap (MS)" in step i) or v), are carried out sequentially within 1 ms to 10 s, wherein the measurement variants TM/VS/REM, that is to say steps ii) to iv) and vi) to viii), may be carried out in any sequence (TM/VS/REM, TM/REM/VS, VS/TM/REM, VS/REM/TM, REM/TM/VS and REM/VS/TM) or in any combination of individual measurement steps (TM/RM, TM/VS, VS/TM, VS/REM, REM/TM, REM/VS).

In the simultaneous measurement variant, the "measuring transmission (TM)" and "measuring forward scattering (VS)" steps or the "measuring transmission (TM)" and "measuring re-emission (REM)" steps are carried out simultaneously, i.e. at the same time.

Therefore, depending on the embodiment of the sensor according to the invention, the present invention relates to a process for quasi-simultaneous measurement of the transmission and/or forward scattering and/or re-emission of a sample and for simultaneous measurement of the transmission and forward scattering or transmission and re-emission of a sample using a sensor according to the invention, said process comprising:

i) formation of a measurement volume with a defined thickness (layer thickness) by adjusting the separation of the measurement windows (MF1) and (MF2) with respect to one another, that is to say the measurement gap (MS), to a defined separation of from 1 to 10 000 μm, preferably from 5 to 5000 μm, particularly preferably from 10 to 500 μm, ii) irradiation of a sample at one or more angles with electromagnetic radiation emitted by a light source (LQ) (REM), the electromagnetic radiation interacting with the sample and a part of the radiation being reflected diffusely and/or specularly after interaction with the sample, and shining electromagnetic radiation emitted by a light source (LQ) (TM/VS) through the sample, the electromagnetic radiation interacting with the sample and a part of the radiation passing through the sample, or being scattered in the forward direction, after interaction with the sample, iii) receiving and registering the diffusely reflected radiation as a re-emission signal (back-scattering) at one or more angles, and receiving and registering the radiation passing through the sample as forward scattering at one or more angles and/or as a transmission signal (transmission) at an angle.

Particularly preferably, the process additionally comprises the following steps:

iv) receiving and registering a reference signal, the reference signal being electromagnetic radiation which is emitted by the same light source (LQ)(REM) as that used for the irradiation of the sample but which does not interact with the sample, and/or receiving and registering a reference signal, the reference signal being electromagnetic radiation which is emitted by the same light source (LQ) (TM/VS) as that used for shining through the sample but which does not interact with the sample, the re-emission signal and the reference signal of (LQ) (REM) being registered simultaneously, and the transmission signal/forward scattering signal and the reference signal of (LQ) (TM/VS) being registered simultaneously.

The effect thereby achieved is that all signals, that is to say the re-emission signals and the reference signal, are subject to the same stochastic variations. This is preferably achieved by using fiber-optic monolithic linear diode array spectrometers, which preferably allow a resolution of at least 15 bits and which are adapted to the existing brightness with integration times of between 4 ms and 6000 ms. The values measured by such linear diode array spectrometers relate to a number of diodes and must be interpolated to fixed wavelengths. This interpolation is particularly accurate when a spline is used, which is preferred.

In a preferred embodiment, the process according to the invention is a continuous process for quasi-simultaneous measurement of the transmission and/or forward scattering and/or re-emission of a flowing sample and for simultaneous measurement of the transmission and forward scattering or transmission and re-emission of a flowing sample, in which the measurement gap is only reduced when required, without significantly reducing the flow through the measurement cell (MZ) itself. That is to say, the supply of the flowing sample need not be interrupted in a continuous measurement operation. Preferably, a continuous process is achieved with the sensor according to the invention, in which the diameter (D) of the measurement window (MF1) or (MF2), preferably (MF2), connected to the plunger is less than the width (d) of the area of the measurement cell (MZ) (cf. FIGS. 2a-d and 3a-b), on which the measurement window (MF1) or (MF2), preferably (MF2), connected to the plunger rests. As a result of the diameter (D) of the measurement window (and consequently of the plunger (ST)) being less than the width (d) of the area of the measurement cell (MZ), the sample channel is not completely closed when driving together the measurement windows (MF1) and (MF2), i.e. when reducing the measurement gap (MS), during which the plunger (ST) is advanced into the measurement cell, but two channels (K) are formed to the left and right of the plunger (ST) in the flow direction, said channels permitting the unimpeded passage of some of the flowing sample introduced into the measurement cell (MZ), as a result of which only some of the flowing sample flows into the measurement gap (MS) between the measurement windows (MF1) and (MF2) and is available for the measurement.

With the aid of the sensor according to the invention and the process according to the invention, accurate and rapid determination of the color properties (for example hiding power, color strength, color locus, angle-dependent color locus) of a sample, for example of painting means such as coatings and paints, pastes and pigments and/or stable dilutions thereof is possible.

Use

In a further embodiment, the present invention relates to use of the sensor according to the invention for quasi-simultaneous measurement of the transmission and/or forward scattering and/or re-emission of a sample and for simultaneous measurement of the transmission and forward scattering or transmission and re-emission of a sample, for determining the color properties of painting means such as coatings and colors, pastes and pigments or the dilutions thereof.

Preferably, the sensor according to the invention is used in any desired process stage during the production, further processing and use of samples in the form of liquid pigment preparations and dilutions thereof, preferably for monitoring the pigment quantities in paints, coatings and pigment pastes; for quality control in the dispersion of pigmented paints, coatings and pigment pastes; for quality assessment during the production of paints, during coating production and during the production of pigment pastes; for controlling a dosing system during the manufacture of coatings, paints and pigment pastes by mixing different liquids/suspensions/emulsions; for automatically regulated color adjustment by tinting during the production of paints; during coating production and during the production of pigment pastes, for color matching of the color of the coating in a coating system which comprises a dosing system for colored pastes and/or for monitoring subsequent color changes due to aging or shear stress of pigmented paints, coatings or pigment pastes; or for checking the optimal grinding factor of transparent and semitransparent pigment pastes. In particular, the sensor according to the invention is suitable for the measurement of coatings for buildings and of base coatings and varnishes in the automobile or OEM sector.

The invention claimed is:

1. A sensor for quasi-simultaneous measurement of at least one of transmission (TM), forward scattering (VS), and re-emission (REM) of a liquid sample, and for simultaneous measurement of one of (i) the transmission (TM) and forward scattering (VS) or (ii) the transmission (TM) and re-emission (REM) of the liquid sample, wherein the sensor is formed from
   a) one or more light sources (LQ)(TM/VS/REM),
   b) one or more illumination optical units (BO),
   c) at least one measurement cell (MZ),
   d) at least one reception optical unit (EO)(TM/VS/REM), and
   e) at least one detector (DET)(TM/VS/REM) for measuring transmission signals generated by transmission, for measuring forward scattering signals generated by forward scattering, and for measuring re-emission signals generated by re-emission,
   wherein the measurement cell (MZ) is a cell that allows flow of the liquid sample therethrough and that comprises two opposing measurement windows (MF1) and (MF2) arranged parallel, wherein the measurement windows (MF1) and (MF2) are arranged with respect to one another in such a way that a measurement gap (MS), which is filled with the liquid sample to be measured, is formed between the measurement windows (MF1) and (MF2), the measurement windows (MF1) and (MF2) having a defined separation from one another that is variably adjustable during a through-flow operation, wherein the defined separation of the measurement windows (MF1) and (MF2) in the through-flow operation is variably adjustable with an accuracy of, on average, 40 to 100 nm, as a standard deviation of the difference between an actual value and an intended value.

2. The sensor as claimed in claim 1, characterized in that at least two measurements selected from transmission (TM), forward scattering (VS) and re-emission (REM) are carried out in combination during the quasi-simultaneous measurement.

3. The sensor as claimed in claim 1, characterized in that the forward scattering signals generated by forward scattering are measured simultaneously using at least two detectors positioned at an angle range of 0° to 90° in relation to a VS light source.

4. The sensor as claimed in claim 3, wherein the forward scattering signals generated by forward scattering are measured simultaneously using at least three detectors.

5. The sensor as claimed in claim 4, wherein the at least three detectors are positioned at angles of 20°, 30°, and 65° in relation to the VS light source.

6. The sensor as claimed in claim 1, characterized in that the re-emission signals generated by re-emission are measured simultaneously using at least three detectors positioned at an angle range of 10° to 115° in relation to a glancing angle of an REM light source.

7. The sensor as claimed in claim 6, wherein the re-emission signals generated by re-emission are measured simultaneously using at least five detectors.

8. The sensor as claimed in claim 7, wherein the at least five detectors are positioned at angles of 15°, 25°, 45°, 75°, and 110° in relation to the glancing angle of the REM light source.

9. The sensor as claimed in claim 1, characterized in that the measurement cell (MZ) is configured in such a way that one of the two measurement windows (MF1) or (MF2) is connected to a movable plunger (ST), wherein a diameter (D) of the measurement window (MF1) or (MF2) connected to the plunger (ST) is less than the width (d) of an area of the measurement cell (MZ) on which the measurement window (MF1) or (MF2) connected to the plunger (ST) rests.

10. The sensor as claimed in claim 9, wherein the measurement cell (MZ) is configured in such a way that the measurement window (MF2) is connected to the movable plunger (ST).

11. The sensor as claimed in claim 1, characterized in that the defined separation of the measurement windows (MF1) and (MF2) is 1 to 10 000 μm.

12. The sensor as claimed in claim 1, characterized in that each of the at least one reception optical units (E0)(TM/VS/REM) are configured independently of one another as a fiber optical system and/or as a conventional system with lenses and stops.

13. The sensor as claimed in claim 1, characterized in that the at least one detector (DET)(TM/VS/REM) is an intensity detector.

14. The sensor as claimed in claim 1, characterized in that the one or more light sources (LQ)(TM/VS/REM), one or more illumination optical units (BO), at least one measurement cell (MZ), at least one reception optical unit (E0)(TM/VS/REM), and at least one detector (DET)(TM/VS/REM) are housed in a common housing, in which there is ventilation and thermostat-regulated heat dissipation.

15. A process for quasi-simultaneous measurement of at least one of transmission (TM), forward scattering (VS) and re-emission (REM) of a liquid sample, and for simultaneous measurement of one of (i) the transmission (TM) and forward scattering (VS) or (ii) the transmission (TM) and re-emission (REM) of the liquid sample using a sensor as claimed in claim 1, said process comprising:
  i) forming a measurement volume with a defined thickness by adjusting the separation of the measurement windows (MF1) and (MF2) to a defined distance of 1 to 10 000 µm,
  ii) irradiating the liquid sample under one or more angles with electromagnetic radiation emitted by an REM light source, wherein the electromagnetic radiation interacts with the sample and some of the electromagnetic radiation is reflected at least one of diffusely and in a directed manner after interaction with the liquid sample, and
  shining electromagnetic radiation emitted by a TM/VS light source through the liquid sample, wherein the electromagnetic radiation interacts with the liquid sample and some of the electromagnetic radiation, after interaction with the liquid sample, shines through the liquid sample or is scattered in the forward direction,
  iii) receiving and registering the diffusely reflected electromagnetic radiation as a re-emission signal at one or more angles, and
  receiving and registering the electromagnetic radiation passing through the liquid sample at least one of (i) as a transmission signal at one angle and (ii) as a forward scattering signal at one or more angles;
  wherein, alternatively, only the transmission signal at one angle is measured simultaneously with the forward scattering signal or the re-emission signal at one or more angles.

16. The process as claimed in claim 15, additionally comprising at least one of the following steps:
  iv) receiving and registering a first reference signal, wherein the first reference signal is electromagnetic radiation which is emitted by the REM light source that serves to irradiate the liquid sample but which does not interact with the liquid sample,
  wherein the re-emission signal and the first reference signal of the REM light source are registered simultaneously, and
  v) receiving and registering a second reference signal, wherein the second reference signal is electromagnetic radiation which is emitted by the TM/VS light source that serves to shine through the liquid sample but which does not interact with the liquid sample,
  wherein the transmission signal/forward scattering signal and the second reference signal of the TM/VS light source are registered simultaneously.

17. The process as claimed in claim 15, characterized in that the process is continuous, such that only some of the liquid sample introduced into the measurement cell (MZ) flows between the measurement windows (MF1) and (MF2) and the remainder of the liquid sample introduced into the measurement cell (MZ) is able to escape from the measurement cell (MZ) without being impeded, said channels being formed by the measurement window (MF1), the plunger (ST), and the measurement cell (MZ).

18. A method for quasi-simultaneous measurement of at least one of transmission (TM), forward scattering (VS), and re-emission (REM) of a liquid sample, and for simultaneous measurement of one of (i) the transmission (TM) and forward scattering (VS) or (ii) the transmission (TM) and re-emission (REM) of a liquid sample, the method comprising using the sensor as claimed in claim 1.

19. The method of claim 18 further comprising using the sensor in any desired process stage during production, further processing, and use of samples in the form of liquid pigment preparations or stable dilutions thereof, preferably for monitoring pigment quantities in paints, coatings, and pigment pastes; for quality control in dispersion of pigmented paints, coatings, and pigment pastes; for quality assessment during production of paints, during coating production, and during production of pigment pastes; for controlling a dosing system during manufacture of coatings, paints, and pigment pastes by mixing different liquids/suspensions/emulsions; for automatically regulated color adjustment by tinting during the production of paints; during coating production and during the production of pigment pastes, for color matching of a color of the coating in a coating system which comprises a dosing system for colored pastes and/or for monitoring subsequent color changes due to aging or shear stress of pigmented paints, coatings or pigment pastes; or for checking an optimal grinding factor of transparent and semitransparent pigment pastes.

* * * * *